United States Patent [19]

Chapman et al.

[11] 4,207,104

[45] Jun. 10, 1980

[54] PHOTOGRAPHIC PRODUCTS AND PROCESSES EMPLOYING NOVEL NONDIFFUSIBLE HETEROCYCLYLAZONAPHTHOL DYE-RELEASING COMPOUNDS

[75] Inventors: Derek D. Chapman, Rochester; E-Ming Wu, Webster, both of N.Y.

[73] Assignee: Eastman Kodak Company, Rochester, N.Y.

[21] Appl. No.: 2,127

[22] Filed: Jan. 9, 1979

Related U.S. Application Data

[63] Continuation-in-part of Ser. No. 832,309, Sep. 12, 1977, abandoned.

[51] Int. Cl.$^2$ .................. G03C 5/54; G03C 1/40; G03C 7/00; G03C 1/10
[52] U.S. Cl. ..................... 430/225; 430/226; 430/505; 430/559
[58] Field of Search ............ 96/3, 29 D, 73, 77, 96/99; 260/146 R, 146 D, 146 T, 147

[56] References Cited

U.S. PATENT DOCUMENTS

| | | | |
|---|---|---|---|
| 4,142,891 | 3/1979 | Baigrie et al. | 96/77 |
| 4,147,544 | 4/1979 | Anderson et al. | 96/77 |

*Primary Examiner*—Richard L. Schilling
*Attorney, Agent, or Firm*—Harold E. Cole

[57] ABSTRACT

Photographic elements, diffusion transfer assemblages and processes are described which employ a novel nondiffusible compound having a releasable 2-(2-heterocyclylazo)-1-naphthol dye moiety which contains a nitrogen atom adjacent to the point of attachment to the azo linkage. The compound contains a ballasted carrier moiety which is capable of releasing the diffusible azo dye under alkaline conditions. The dye is transferred imagewise to an image-receiving layer where it is contacted with metal ions to form a metal-complexed azo dye transfer image of excellent stability.

36 Claims, No Drawings

PHOTOGRAPHIC PRODUCTS AND PROCESSES EMPLOYING NOVEL NONDIFFUSIBLE HETEROCYCLYLAZONAPHTHOL DYE-RELEASING COMPOUNDS

This application is a continuation-in-part of our co-pending U.S. application Ser. No. 832,309, filed Sept. 12, 1977, now abandoned.

This invention relates to photography and more particularly to color diffusion transfer photography employing certain nondiffusible azo dye-releasing compounds which, as a function of development of a silver halide emulsion layer, release a diffusible, metallizable 2-(2-heterocyclylazo)-1-naphthol dye which contains a nitrogen atom adjacent to the point of attachment to the azo linkage. Highly stable metal complexes of this dye are formed in the imagereceiving layer.

Azo dye developers containing metallizable groups are disclosed in U.S. Pat. Nos. 3,081,167; 3,196,014; 3,299,041; 3,453,107; 3,563,739; 3,544,545 and 3,551,406. Since it is a reactive species, however, the developer moiety of such dye developers is capable of developing any exposed silver halide emulsion layer with which it comes into contact, rather than just developing the adjacent silver halide emulsion with which it is associated. Unwanted wrong-layer development, therefore, can occur in dye developer systems which results in undesirable interimage effects. Accordingly, it is desirable to provide an improved transfer system in which the dye is not attached to a "reactive" moiety, such as a developer moiety, so that such dye can diffuse throughout the photographic film unit without becoming immobilized in undesired areas.

In U.S. Pat. No. 4,076,529, issued Feb. 28, 1978, nondiffusible dye-releasing compounds are disclosed. Among the various dye moieties disclosed which can be released are "metal complexed dyes". No specific structures are shown, however.

Anderson and Nickless, Analyst 93, 13 and 20 (1968) describe pyridylazo and pyrimmidylazonaphthol dyes as colorimetric indicators for the analytical determination of metal ions such as copper. The compounds employed in the instant invention nor their use in photographic products are not shown, however.

In U.S. Pat. Nos. 3,931,144; 3,932,380; 3,942,987; 3,954,476; 4,001,209; 4,013,633 and 4,013,635, various nondiffusible azo dye-releasing compounds are disclosed. The released dyes, however are not disclosed as being metallized or metallizable.

The April 1977 edition of Research Disclosure, pages 32 through 39, discloses various nondiffusible dyereleasing compounds and various metallized azo dye fragments. Such premetallized dyes are large molecules which diffuse more slowly than unmetallized dyes, resulting in long access times for image formation. In any event, however, the specific compounds employed in the instant invention are not disclosed.

U.S. Pat. Nos. 3,086,005; 3,492,287 and 3,985,499 disclose various azo dyes, U.S. Pat. Nos. 2,348,417; 2,495,244; and 2,830,042 and French Pat. Nos. 1,124,882 and 1,200,358 disclose various dyes from azopyridines, while U.S. Pat. Nos. 2,868,775; 2,938,895; 3,097,196; 3,691,161; and 3,875,139; British Pat. No. 899,758; and an article entitled "The Irgalan Dyes—Neutral-Dyeing Metal-Complex Dyes" by Guido Schetty, J. Soc. Dyers and Colourists, Volume 71, 1955, pages 705 through 724, disclose various metal complexed dyes. Again, however, neither the specific compounds employed in the instant invention nor the results obtained therewith are disclosed.

In U.S. Pat. No. 4,142,891 of Baigrie et al, issued Mar. 6, 1979, there is a generic description of metallizable compounds which include those of the instant invention. The compounds of the instant invention are not specifically taught by Baigrie et al, however, and the results obtained with the instant invention are unexpectedly superior, as described below.

It would be desirable to provide improved dye-releasing compounds containing chelating dye moieties, so that the dye which is released imagewise during processing can diffuse to an image-receiving layer containing metal ions to form a metal-complexed, dye transfer image having better hues, rapid diffusion rates and shorter access times than those of the prior art, as well as good stability to heat, light and chemical reagents. The dyes of the present invention, when chelated by metal ions such as nickel (II) ions, have a good magenta or cyan due with minimal unwanted absorption. They have superior stability to fading by light in a variety of environments. The absorption of the non-diffusible compounds of the present invention in a photographic element before processing is, to a large extent, shifted out of the desired region of the spectrum, particularly at low pHs. When the released dye is metallized in a receiving element, however, a magenta or cyan dye with excellent hue for use in color photography is produced.

A photographic element in accordance with the invention comprises a support having thereon at least one photosensitive silver halide emulsion layer having associated therewith a nondiffusible compound having at least one releasable 2-(2-heterocyclylazo)-1-naphthol dye moiety, said compound containing a ballasted carrier moiety which is capable of releasing said diffusible azo dye under alkaline conditions, such as, for example, as a function (either direct or inverse) of development of the silver halide emulsion layer, the heterocyclyl moiety containing a nitrogen atom adjacent to the point of attachment to the azo linkage.

Good dyes may be obtained in a preferred embodiment of the invention when the 2-(2-heterocyclylazo)-1-naphthol dye-releasing compound is represented by the formula:

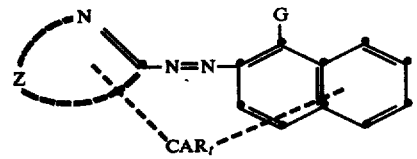

wherein:

G is a hydroxy group or a salt thereof (e.g., a sodium salt, a tetramethylammonium salt, etc,) or a hydrolyzable precursor thereof (e.g., an acyloxy group having the formula $-OCOR^1$, $-OCOOR^1$, or $-OCON(R^1)_2$, wherein each $R^1$ is an alkyl group having 1 to about 8 carbon atoms, such as methyl, ethyl, isopropyl, butyl and the like, or an aryl group having 6 to about 12 carbon atoms, such as phenyl, etc;) or a group which together with

is CAR which is bonded to the naphthalene group through the oxygen of the

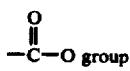

(the oxygen being bonded directly to the naphthalene ring);

Z represents the atoms necessary to complete a heterocyclic ring;

CAR represents said ballasted carrier moiety; and t is a positive integer of 1 to 2.

Z in the above formula, together with the nitrogen atom to which it is attached, can represent a wide variety of heterocyclic rings, such as pyridine, pyrimidine, quinoline, isoquinoline, pyrazine, pyridazine, thiazole, thiadiazole, triazole, benzothiazole, acinaphthothiazole, etc. In general, Z and the nitrogen atom to which it is attached are an aromatic or non-aromatic, 5- or 6-membered heterocyclic nitrogen-containing ring. In a preferred embodiment, the ring is aromatic. In another preferred embodiment, the ring contains six members. This ring may also have other rings fused thereon.

In still another preferred embodiment of the invention, t is 1, G is OH and Z represents the atoms necessary to complete a pyridine or pyrimidine ring.

Other substituents may also be present in either of the two ring systems in the formula above, such as alkyl of 1 to 6 carbon atoms, alkoxy, halogens, solubilizing groups such as sulfonamido, sulfamoyl, carbamoyl, alkoxycarbonyl, carboxy, sulfo, hydrolyzable precursors thereof, etc. The heterocyclic ring may not be substituted with a nitro group, however.

In another preferred embodiment of the invention, CAR may have attached thereto two azo dye moieties as shown by the formula above, in which case two dye moieties will be released from one CAR moiety.

When hydrolyzable precursors of the dye moiety of the above compounds are employed, the absorption spectrum of the azo dye is shifted to shorter wavelengths. "Shifted dyes" of this type absorb light outside the range to which the associated layer halide layer is sensitive. In some cases, the absorption spectrum of the unmetallized azo dye ligand is substantially shifted to shorter wavelengths at neutral pH (e.g., 5 to 8).

There is great latitude in selecting a CAR moiety which is attached to the 2-(2-heterocyclylazo)-1-naphthol dye-releasing compounds described above. Depending upon the nature of the ballasted carrier selected, various groups may be needed to attach or link the carrier moiety to the dye. Such linking groups are considered to be a part of the CAR moiety in the above definition. It should also be noted that when the dye moiety is released from the compound, cleavage may take place in such a position that part or all of a linking group if one is present, and even part of the ballasted moiety may be transferred to the image-receiving layer along with the dye moiety. In any event, the dye nucleus as shown above can be thought of as the "minimum" which is transferred.

CAR moieties useful in the invention are described in U.S. Pat. Nos. 3,227,550; 3,628,952; 3,227,552; and 3,844,785 (dye released by chromogenic coupling); U.S. Pat. Nos. 3,443,939 and 3,443,940 (dye released by intramolecular ring closure); U.S. Pat. No. 3,698,897 and 3,725,062 (dye released from hydroquinone derivatives; U.S. Pat. No. 3,728,113 (dye released from a hydroquinoylmethyl quaternary salt); U.S. Pat. Nos. 3,719,489 and 3,443,941 (silver ion induced dye released); and U.S. Pat. Nos. 3,245,789 and 3,980,497; Canadian Patent 602,607; British Pat. No. 1,464,104; 14447, April 1976; U.S. Pat. No. 4,139,379, issued Feb. 13, 1979 of Chasman el al (dye released by miscellaneous mechanisms), the disclosures of which are hereby incorporated by reference.

In a further preferred embodiment of the invention, the ballasted carrier moiety or CAR as described above may be represented by the following formula:

(Ballast-Carrier-Link)— wherein:

(a) Ballast is an organic ballasting radical of such molecular size and configuration as to render the compound nondiffusible in a photographic element during development in an alkaline processes composition;

(b) Carrier is an oxyidizable acyclic, carboxylic or heterocyclic moiety (see "The Theory of the Photographic Process", by C. E. K. Mees and T. H. James, Third Edition, 1966, pages 282 to 283), e.g., moieties containing atoms according to the following configuration:

wherein:

b is a positive integer of 1 to 2; and a represents the radicals OH, SH, NH$_{13}$, or hydrolyzable precursors thereof; and (c) Link represents a group which upon oxidation of said Carrier moiety is capable of being hydrolytically cleaved to release the diffusible azo dye. For example, Link may be the following groups:

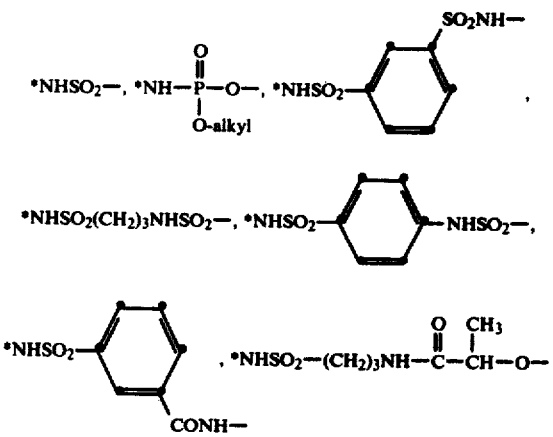

wherein * represents the position of attachment to Carrier.

The Ballast group in the above formula is not critical as long as it confers nondiffusibility to the compound. Typical Ballast groups include long-chain alkyl radicals linked directly or indirectly to the compound as well as aromatic radicals of the benzene and naphthalene series indirectly attached or fused directly to the ring, etc. Useful Ballast groups generally have at least 8 carbon atoms such as substituted or unsubstituted alkyl groups of 8 to 22 carbon atoms, a carbamoyl radical having 8 to 30 carbon atoms such as —CONH(CH$_2$)$_4$—O—C$_6$H$_3$(C$_5$H$_{11}$)$_2$, —CON(C$_{12}$H$_{25}$)$_2$, etc, a keto radical having 8 to 30 carbon atoms such as —CO—C₁₇H₃₅, —CO—C₆H₄(t—C₁₂H₂₅), etc.

For specific examples of Ballast-Carrier-Link moieties useful as the CAR moiety in this invention, reference is made to the November 1976 edition of *Research Disclosure*, pages 68 through 74, and the April 1977 edition of *Research Disclosure*, pages 32 through 39, the disclosures of whidch are hereby incorporated by reference.

In a highly preferred embodiment of the invention, the ballasted carrier moiety or CAR in the above formulas is a group having the formula:

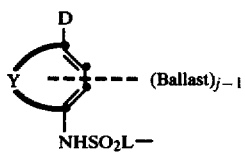

wherein:

(a) Ballast is an organic ballasting radical of such molecular size and configuration (e.g., simple organic groups or polymeric groups) as to render the compound non-diffusible in a photographic element during development in an alkaline processing composition:

(b) D is OR² or NHR³ wherein R² is hydrogen or a hydrolyzable moiety and R³ is hydrogen or a substituted or unsubstituted alkyl group of 1 to 22 carbon atoms such as methyl, ethyl, hydroxyethyl, propyl, butyl, secondary butyl, tert-butyl, cyclopropyl, 4-chlorobutyl, cyclobutyl, 4-nitroamyl, hexyl, cyclohexyl, octyl, decyl, octadecyl, dodecyl, benzyl, phenethyl, etc. (when R³ is an alkyl group of greater than 8 carbon atoms, it can serve as a partial or sole Ballast);

(c) Y represents the atoms necessary to complete a benzene nucleus, a naphthalene nucleus, or a 5 to 7 membered heterocyclic ring such as pyrazolone, pyrimidine, etc;

(d) j is a positive integer of 1 to 2and is 2 when D is OR² or when R³ is hydrogen or an alkyl grup of less than 8 carbon atoms; and (e) L is a linking group which is [X—(NR⁴—J)$_q$-]$_m$— or X—J—NR⁴— wherein:
  (i) represents a bivalent linking group of the formula —R⁵—L′$_n$R⁵$_p$ where each R⁵ can be the same or different and each represents an alkylene radical of having 1 to about 8 carbon atoms, such as methylene, hexylene and the like; a phenylene radical; or a substituted phenylene radical having 6 to about 9 carbon atoms, such as methoxy phenylene;
  (ii) L′ represents a bivalent radical selected from oxy, imino, carbonyl, carboxamido, carbamoyl, sulfonamido, urethylene, sulfaoyl, sulfinyl or sulfony;
  (iii) n is an integer of 0 or 1;
  (iv) p is 1 when n equals 1 and p is 1 or 0 when n equals 0, provdied that when p is 1 the carbon content of the sum of both R⁵ radicals does not exceed 14 arbon atoms;
  (v) R⁴ represents a hydrogen atom, or an alkyl radical having 1 to about 6 carbon atoms;
  (vi) J represents a bivalent radical selected from sulfonyl or carbonyl;
  (vii) q represents an integer of 0 or 1; and
  (viii) m represents an integer of 0, 1 or 2.

Especially good results are obtained in the above formula when D is OH, j is 2, and Y is a naphthalene nucleus.

Examples of the CAR moiety in this highly preferred embodiment are disclosed in U.S. Pat. No. 4,076,529 U.S. Pat. No. 3,928,312; French Pat. No. 2,284,140; and German Pat. Nos. 2,406,664; 2,613,005; and 2,505,248, the disclosures of which are hereby incorporated by reference, and include the following:

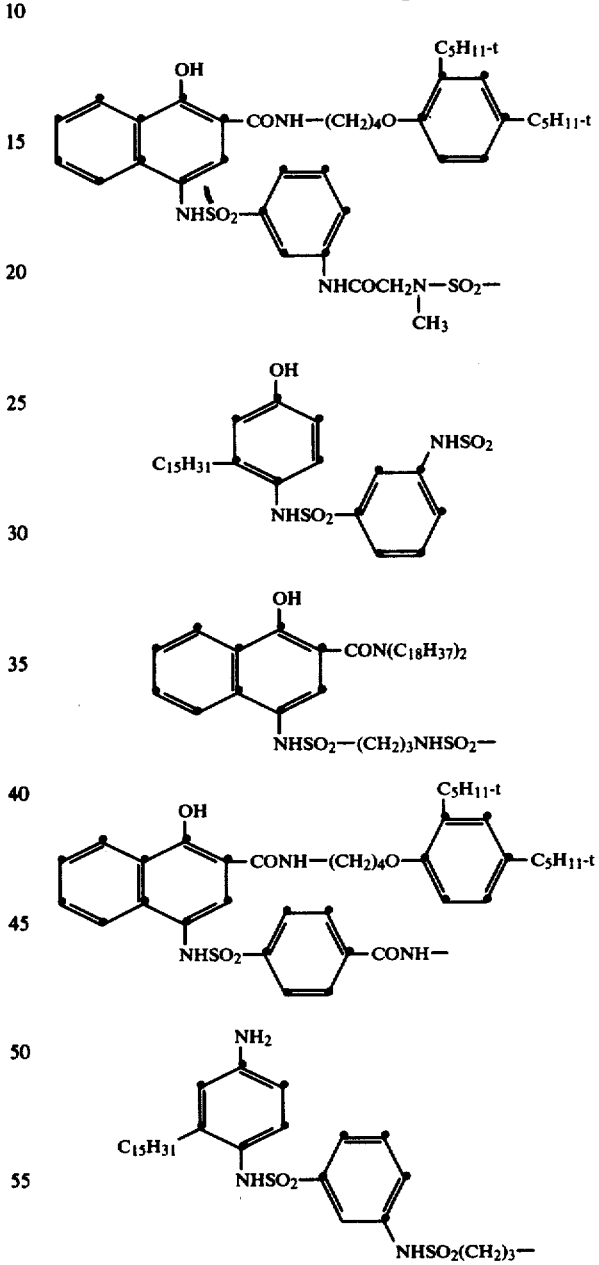

In another highly preferred embodiment of the invention, the ballasted carrier moiety or CAR in the above formulas is such that the diffusible azo dye is released as an inverse function of development of the silver halide emulsion layer under alkaline conditions. This is ordinarily referred to as positive-working dye-release chemistry. In one of these embodiments, the ballasted carrier moiety or CAR in the above formulas may be a group having the formula:

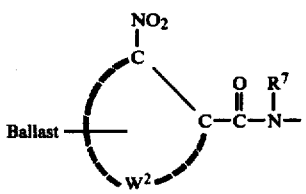

wherein:

Ballast is an organic ballasting radical of such molecular size and configuration as to render the compound nondiffusible in a photographic element during development in an alkaline processing composition;

$W^2$ represents at least the atoms necessary to complete a benzene nucleus (including various substitutents thereon); and $R^7$ is an alkyl (including substituted alkyl) radical having 1 to about 4 carbon atoms.

Examples of the CAR moiety in this formula I include the following:

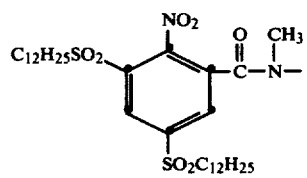

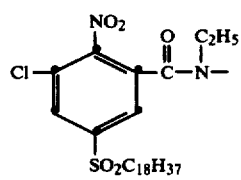

In a second embodiment of positive-working dye-release chemistry as referred to above, the ballasted carrier moiety or CAR in the above formulas may be a group having the formula:

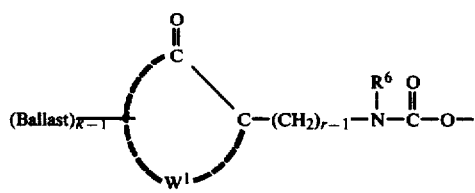

wherein:

Ballast is an organic ballasting radical of such molecular size and configuration as to render the compound nondiffusible in a photographic element during development in an alkaline processing composition;

$W^1$ represents at least the atoms necessary to complete a quinone nucleus (including various substituents thereon);

r is a positive integer of 1 or 2;

$R^6$ is an alkyl (including substituted alkyl) radical having 1 to about 40 carbon atoms or an aryl (including substituted aryl) radical having 6 to about 40 carbon atoms; and k is a positive integer of 1 to 2 and is 2 when $R^6$ is a radical of less than 8 carbon atoms.

Examples of the CAR moiety in this formula II include the following:

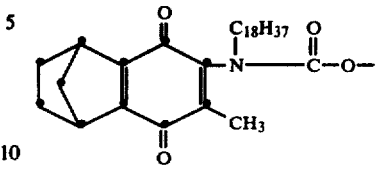

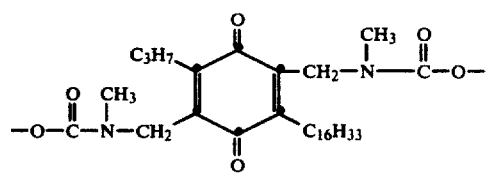

In using the compounds in formulas I and II above, they are employed in a photographic element similar to the other nondiffusible dye-releasers described previously. Upon reduction of the compound as a function of silver halide development under alkaline conditions, the metallizable azo dye is released. In this embodiment, conventional negative-working silver halide emulsions, as well as direct-positive emulsions, can be employed. For further details concerning these particular CAR moieties, including synthesis details, reference is made to U.S. Pat. No. 4,139,379 of Chasman et al, issued Feb. 13, 1979, the disclosure of which is hereby incorporated by reference.

In a third embodiment of positive-working dye-release chemistry as referred to above, the ballasted carrier moiety or CAR in the above formulas may be a group having the formula:

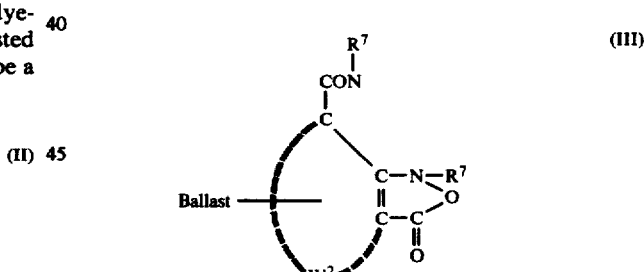

wherein:

Ballast, $W^2$ and $R^7$ are as defined for formula I above.

Examples of the CAR moiety in this formula III include the following:

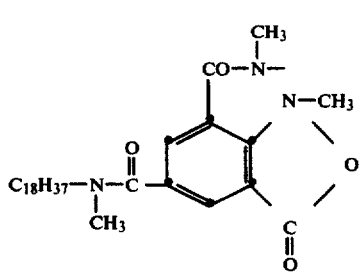

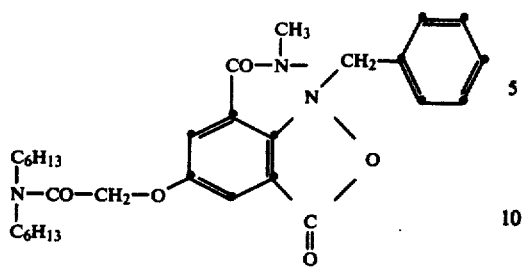

For further details concerning this particular CAR moiety, including synthesis details, reference is made to commonly assigned copending U.S. application Ser. No. 534,966 of Hinshaw et al, filed Dec. 20, 1974, the disclosure of which is hereby incorporated by reference.

In a fourth embodiment of positive-working dye-release chemistry as referred to above, the ballasted carrier moiety or CAR in the above formulas may be a group having the formula:

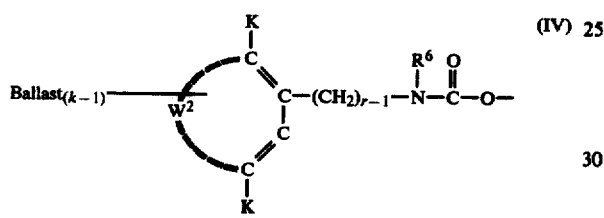

(IV)

wherein:

Ballast, r, $R^6$ and k are as defined for formula II above;

$W^2$ is as defined for formula I above; and

K is OH or a hydrolyzable precursor thereof.

Examples of the CAR moiety in this formula IV include the following:

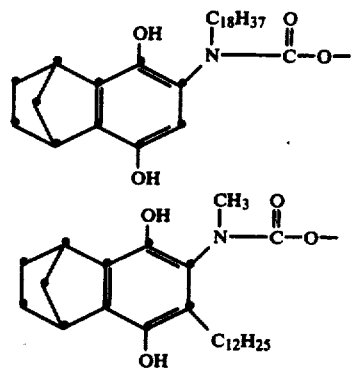

For further details concerning this particular CAR moiety, including synthesis details, reference is made to U.S. Pat. No. 3,980,479 of Fields et al, issued Sept. 14, 1976, the disclosure of which is hereby incorporated by reference.

A bivalent linking group, e.g., L or X as defined above, may be used, if desired, to link the CAR moiety described in formulas I through IV above to the dye moiety previously described.

Representative compounds included within the scope of the invention include the following:

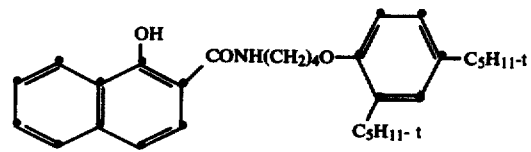

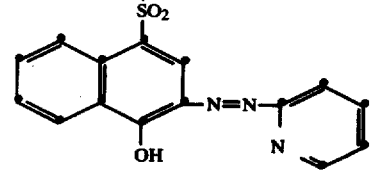

(1)

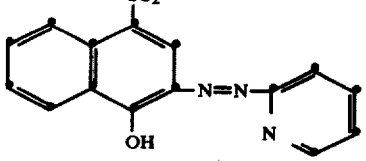

(2)

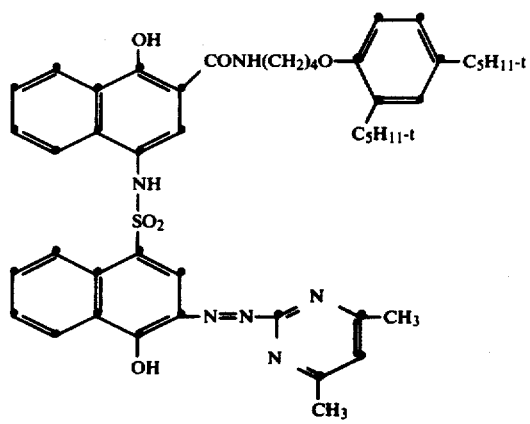
(3)
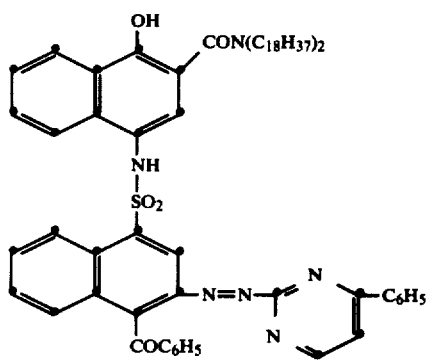
(4)
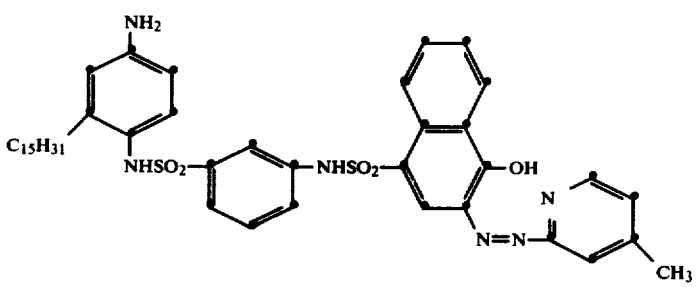
(5)
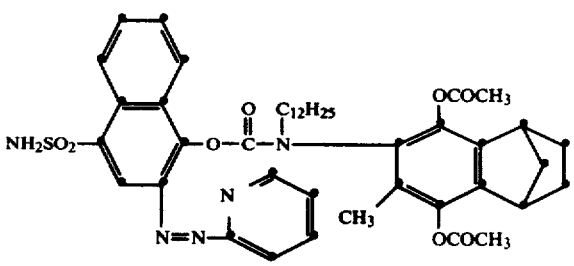
(6)
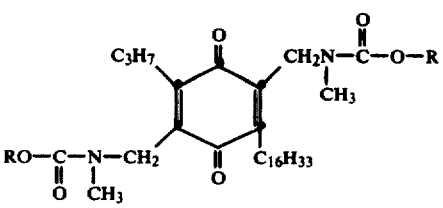
(7)

-continued
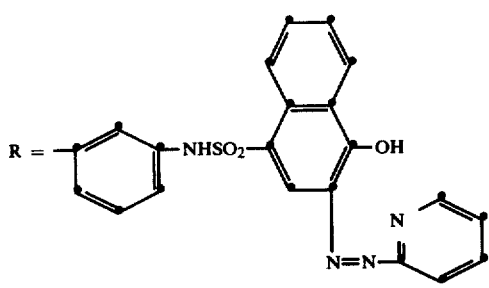
(8)
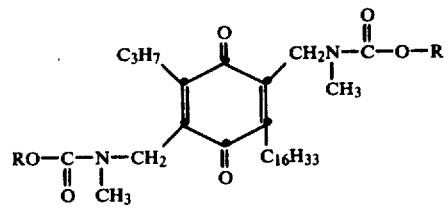
(9)
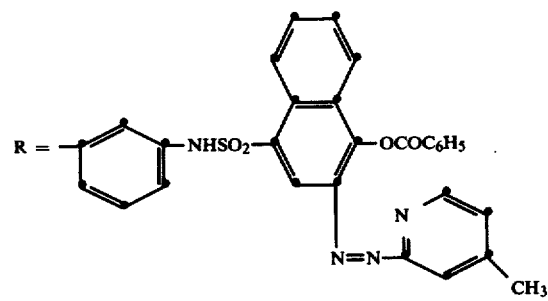
(10)
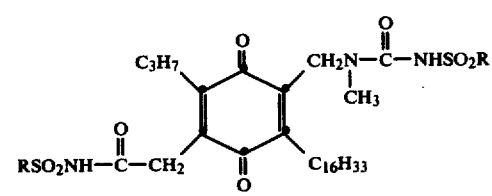
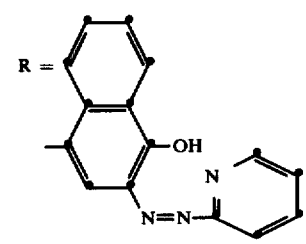
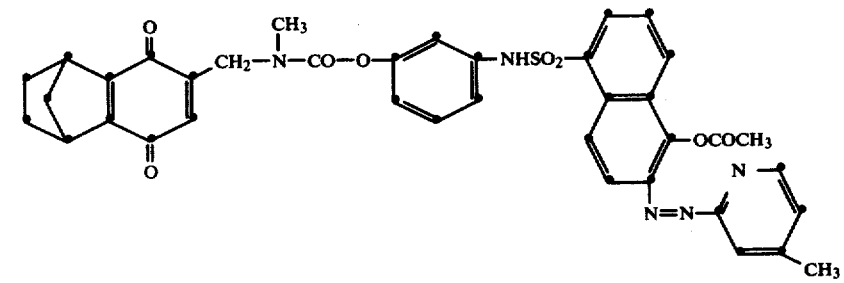
(11)
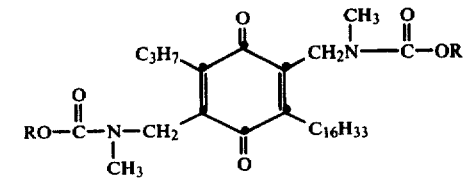

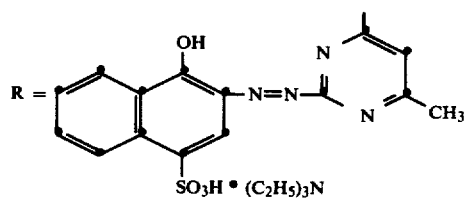
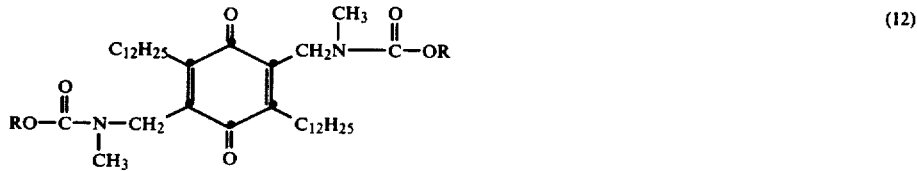
(12)
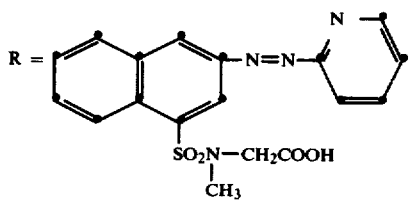
(13)
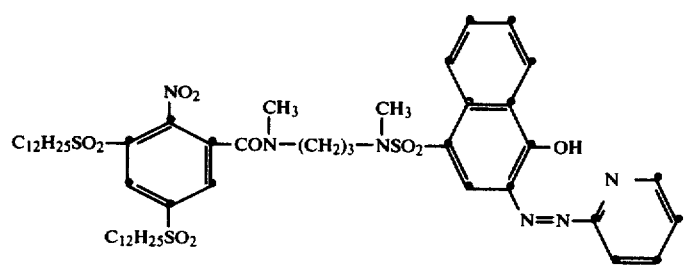
(14)
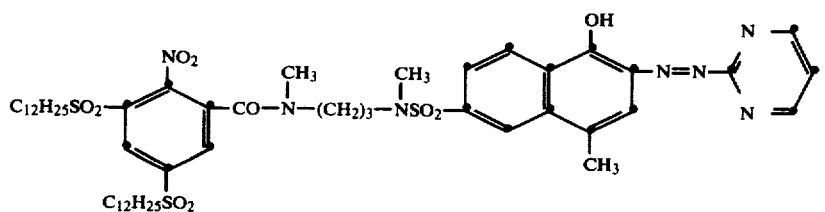
(15)
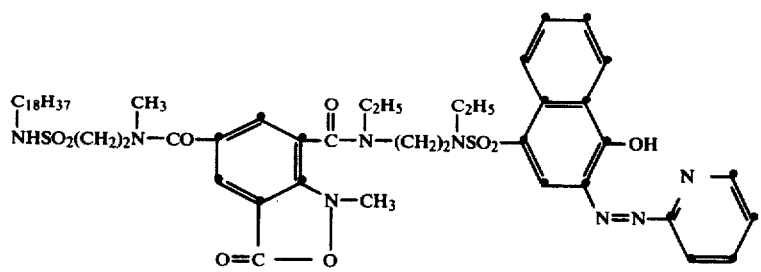
(16)
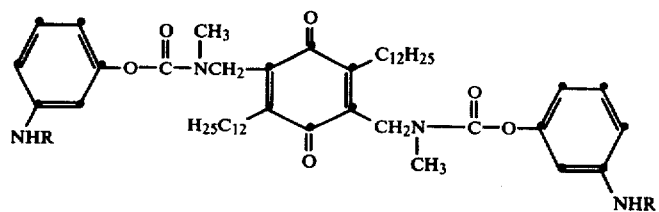

-continued
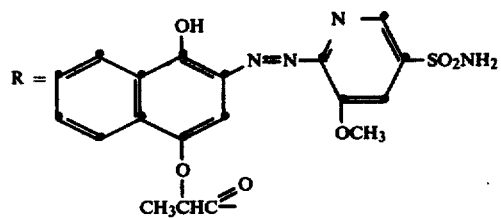
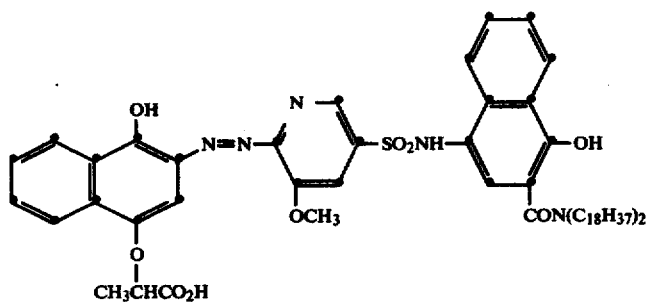
(17)
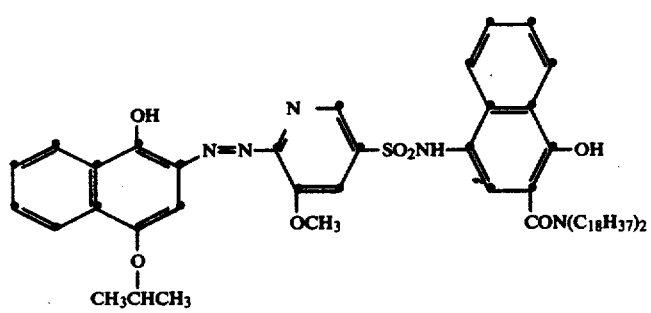
(18)
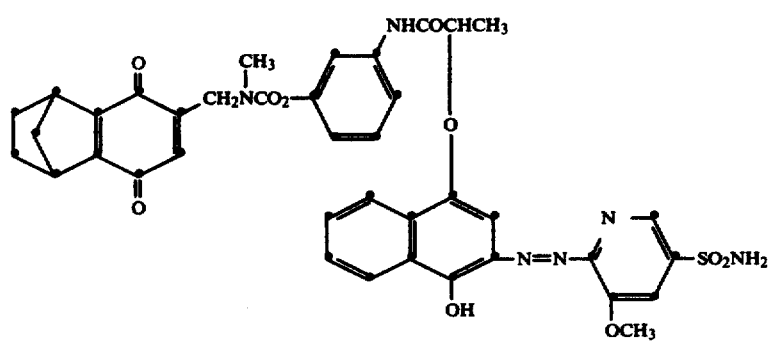
(19)
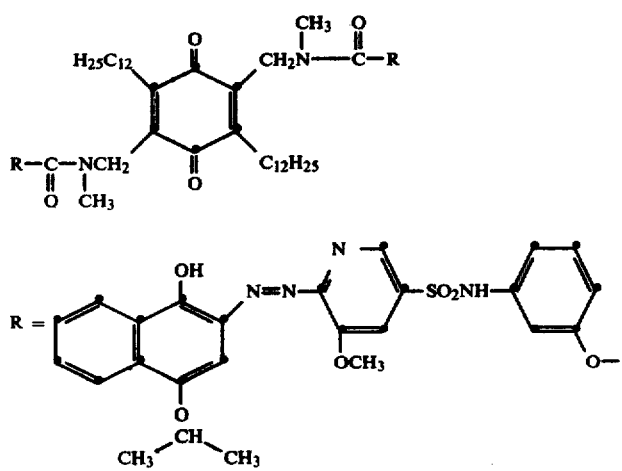
(20)

-continued
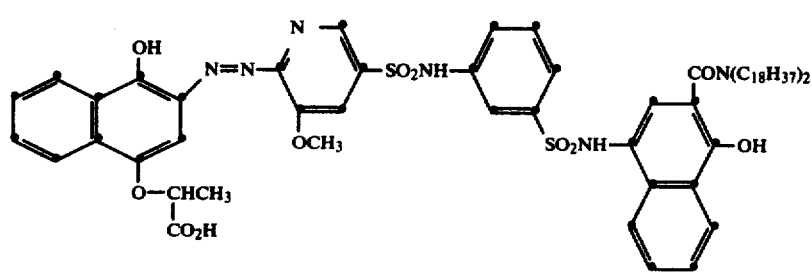
(21)
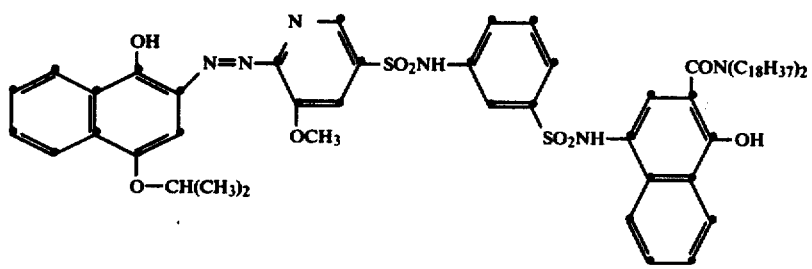
(22)
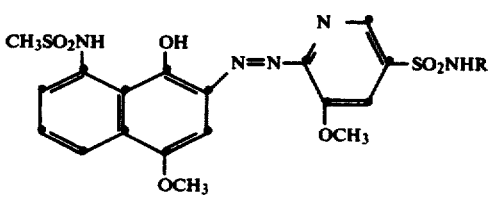
(23)
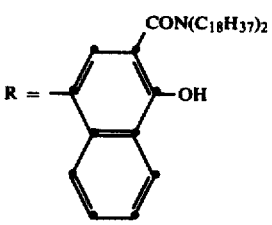
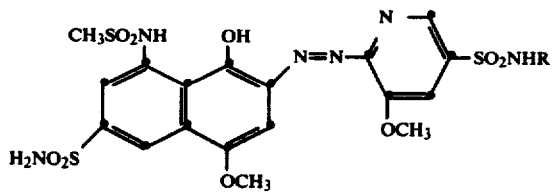
(24)
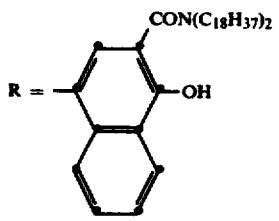
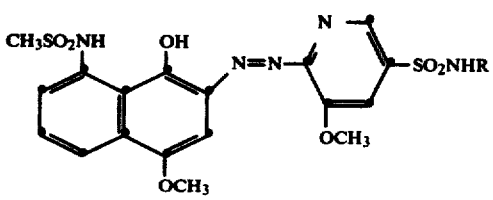
(25)

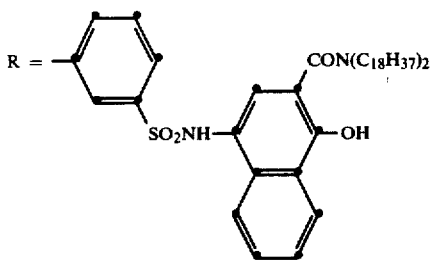

A process for producing a photographic transfer image in color according to the invention comprises:

(a) treating an imagewise-exposed photographic element as described above with an alkaline processing composition in the presence of a silver halide developing agent to effect development of each of the exposed silver halide emulsion layers, (b) the dye-releasing compound then releasing the diffusible azo dye as described above imagewise as a function of the development of each of the silver halide emulsion layers, (c) at least a portion of the imagewise distribution of the azo dye diffusing to a dye image-receiving layer; and (d) contacting the imagewise distribution of azo dye with metal ions, thereby forming a metal-complexed azo dye transfer image.

In another preferred embodiment of the invention, a process for producing a photographic transfer image in color according to the invention comprises:

(a) treating an imagewise-exposed photographic element as described above wherein CAR in the compound has the formula:

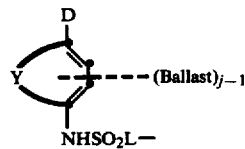

D, Y, L and j being defined as above,
with an alkaline processing composition in the presence of a silver halide developing agent to effect development of each of the exposed silver halide emulsion layers, thereby oxidizing the developing agent;

(b) the oxidized developing agent thereby cross-oxidizing the dye-releasing compound;

(c) the cross-oxidized dye-releasing compound then cleaving as a result of alkaline hydrolysis to release the diffusible azo dye imagewise as a function of the imagewise exposure of each of the silver halide emulsion layers;

(d) at least a portion of the imagewise distribution of the azo dye diffusing to a dye image-receiving layer; and (e) contacting the imagewise distribution of azo dye with metal ions, thereby forming a metal-complexed azo dye transfer image.

The tridentate azo dye ligand which is released from the dye-releasing compounds in accordance with the present invention will form a coordination complex in the image-receiving layer with polyvalent metal ions. The metal ions can be present in the image-receiving layer itself or in a layer adjacent thereto or the image-receiving layer can be contacted with metal ions in a bath after diffusion of the dye has taken place. Metal ions most useful in the invention are those which are essentially colorless when incorporated into the image-receiving element, are inert with respect to the silver halide layers, react readily with the released dye to form a complex of the desired hue, are tightly coordinated to the dye in the complex, have a stable oxidation state, and form a dye complex which is stable to heat, light and chemical reagents. In general, good results are obtained with polyvalent metal ions such as copper (II), zinc (II), nickel (II), platinum (II), palladium (II) and cobalt (II) ions.

For example, it is believed that the coordination complex which is formed from the tridentate azo dye ligand according to the invention in one of the preferred embodiments thereof has the following structure:

Lig

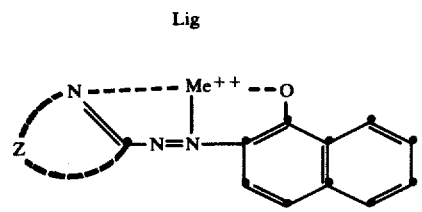

where Z is as defined previously, Me is metal and Lig is one or more ligand groups depending upon the coordination number of the metal ion, such as $H_2O$, Cl, pyridine, etc.

Thus, in accordance with another embodiment of the invention, a photographic element is provided which comprises a support having thereon a coordination complex of a polyvalent metal ion and a compound having the formula:

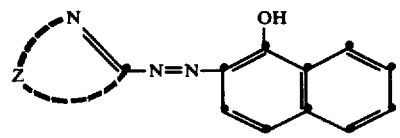

wherein Z is as described above. The element usually contains a photographic mordant or image-receiving layer to bind the dye or coordination complex thereto. The structures shown above may also, of course, be substituted in the same manner as described above for the starting compounds from which they are released, e.g., the heterocyclic ring Z may be substituted in the 3-position with a methyl group, etc.

It will be appreciated that, after processing the photographic element described above, there remains in it after transfer has taken place an imagewise distribution of azo dye in addition to developed silver. A color image comprising residual nondiffusible compound may be obtained in this element if the residual silver and silver halide are removed by any conventional manner well known to those skilled in the photographic art, such as a bleach bath followed by a fix bath, a bleach-fix bath, etc. Such a retained dye image should normally be treated with metal ions to metallize the dyes to increase their light fastness and shift their spectral absorption to the intended region. The imagewise distribution of azo dye may also diffuse out of the element into these baths, if desired, rather than to an image-receiving element. If a negative-working silver halide emulsion is employed in certain preferred photosensitive elements, described above, then a positive color image, such as a reflection print, a color transparency or motion picture film, may be produced in this manner. If a direct-positive silver halide emulsion is employed in such photosensitive elements, then a negative color image may be produced.

The photographic element in the above-described process can be treated with an alkaline processing composition to effect or initiate development in any manner. A preferred method for applying processing composition is by use of a rupturable container or pod which contains the composition. In general, the processing composition employed in this invention contains the developing agent for development, although the composition could also just be an alkaline solution where the developer is incorporated in the photographic element, image-receiving element or process sheet, in which case the alkaline solution serves to activate the incorporated developer.

A photographic film unit which can be processed in accordance with this invention is adapted to be processed by passing the unit between a pair of juxtaposed pressure-applying members, such as would be found in a camera designed for in-camera processing, and comprises:

(1) a photographic element as described above;
(2) a dye image-receiving layer; and
(3) means for discharging an alkaline processing composition within the film unit, such as a rupturable container which is adapted to be positioned during processing of the film unit so that a compressive force applied to the container by the pressure-applying members will effect a discharge of the container's contents within the film unit;

the film unit containing a silver halide developing agent.

In the embodiment described above, the dye image-receiving layer may itself contain metal ions or the metal ions may be present in an adjacent layer, so that the tridentate azo dye ligand which is released will form a coordination complex therewith. The dye thus becomes immobilized in the dye image-receiving layer and metallized at the same time. Alternatively, the dye image in the dye image-receiving layer may be treated with a solution containing metal ions to effect metallization. The formation of the coordination complex shifts the absorption of the dye to the desired hue, usually to longer wavelengths, which have a different absorption than that of the initial dye-releasing compound. If this shift is large enough, then the dye-releasing compound may be incorporated in a silver halide emulsion layer without adversely affecting its sensitivity.

The dye image-receiving layer in the above-described film unit can be located on a separate support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film unit can also be located integral with the photographic element between the support and the lowermost photosensitive silver halide emulsion layer. One useful format for integral receiver-negative photographic elements is disclosed in Belgian Pat. No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer and dye images are formed as a function of development which diffuse to the image-receiving layer to provide a positive, right-reading image which is viewed through the transparent support on the opaque reflecting layer background. For other details concerning the format of this particular integral film unit, reference is made to the above-mentioned Belgian Pat. No. 757,960.

Another format for integral negative-receiver photographic elements in which the present invention can be employed is disclosed in Belgian Pat. No. 757,959. In this embodiment, the support for the photographic element is transparent and is coated with the image-receiving layer, a substantially opaque, light-reflective layer and the photo-sensitive layer or layers described above. A rupturable container containing an alkaline processing composition and an opacifier is positioned adjacent the top layer and a transparent top sheet which has thereon a neutralizing layer and a timing layer. The film unit is placed in a camera, exposed through the transparent top sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images are formed as a result of development which diffuse to the image-receiving layer to provide a positive, right-reading image which is viewed through the transparent support on the opaque reflecting layer background. For further details concerning the format of this particular integral film unit, reference is made to the above-mentioned Belgian Pat. No. 757,959.

Still other useful integral formats in which this invention can be employed are described in U.S. Pat. Nos. 3,415,644; 3,415,645; 3,415,646; 3,647,437; and 3,635,707. In most of these formats, a photosensitive silver halide emulsion is coated on an opaque support and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Pat. No. 904,364, page 19, lines 1 through 41. In this process, the dye-releasing compounds are used in combination with physical development nuclei in a nuclei layer contiguous to the photosensitive silver halide negative emulsion layer. The film unit contains a silver halide solvent, preferably in a rupturable container with the alkaline processing composition.

The film unit or assembly used in the present invention may be used to produce positive images in single- or multicolors. In a three-color system, each silver halide emulsion layer of the film assembly will have associated therewith a dye-releasing compound which releases a dye possessing a predominant spectral absorption within the region of the visible spectrum to which said silver halide emulsion is sensitive (initially or after forming the coordination complex), i.e., the blue-sensitive silver halide emulsion layer will have a yellow or yellow-forming dye-releaser associated therewith, the green-sensitive silver halide emulsion layer will have a magenta or magenta-forming dye-releaser associated therewith, and the red-sensitive silver halide emulsion layer will have a cyan or cyan-forming dye-releaser associated therewith, at least one of the dye-releasers being a compound in accordance with the present invention. The dye-releaser associated with each silver halide emulsion layer may be contained either in the silver halide emulsion layer itself or in a layer contiguous to the silver halide emulsion layer.

The concentration of the dye-releasing compounds that are employed in the present invention may be varied over a wide range, depending upon the particular compound employed and the results which are desired. For example, the dye-releasers of the present invention may be coated in layers by using coating solutions containing between about 0.5 and about 8 percent by weight of the dye-releaser distributed in a hydrophilic film-forming natural material or synthetic polymer, such as gelatin, polyvinyl alcohol, etc, which is adapted to be permeated by aqueous alkaline processing composition.

Depending upon which CAR is used in the present invention, a variety of silver halide developing agents can be employed. In certain embodiments of the invention, any silver halide developing agent can be employed as long as it cross-oxidizes with the dye-releasers described herein. The developer may be employed in the photosensitive element to be activated by the alkaline processing composition. Specific examples of developers which can be employed in this invention include:

N-methylaminophenol
Phenidone (1-phenyl-3-pyrazolidone)
Dimezone (1-phenyl-4,4-dimethyl-3-pyrazolidone)
aminophenols
1-phenyl-4-methyl-4-hydroxymethyl-3-pyrazolidone
N,N-diethyl-p-phenylenediamine
N,N,N',N'-tetramethyl-p-phenylenediamine
3-methyl-N,N-diethyl-p-phenylenediamine
3-methoxy-N-ethyl-N-ethoxy-p-phenylenediamine, etc.

The non-chromogenic developers in this list are preferred, however, since they avoid any propensity of staining the dye image-receiving layer.

In a preferred embodiment of the invention, the silver halide developer employed in the process becomes oxidized upon development and reduces silver halide to silver metal. The oxidized developer then cross-oxidizes the dye-releasing compound. The product of cross-oxidation then undergoes alkaline hydrolysis, thus releasing an imagewise distribution of diffusible azo dye which then diffuses to the receiving layer to provide the dye image. The diffusible moiety is transferable in alkaline processing composition either by virtue of its self-diffusivity or by its having attached to it one or more solubilizing groups, for example, a carboxy, sulpho, sulphonamido, hydroxy or mopholino group.

In using the dye-releasing compounds according to the invention which produce diffusible dye images as a function of development, either conventional negative-working or direct-positive silver halide emulsions may be employed. If the silver halide emulsion employed is a direct-positive silver halide emulsion, such as an internal-image emulsion designed for use in the internal image reversal process or a fogged, direct-positive emulsion such as a solarizing emulsion, which is developable in unexposed areas, a positive image can be obtained in certain embodiments on the dye image-receiving layer. After exposure of the film unit, the alkaline processing composition permeates the various layers to initiate development of the exposed photosensitive silver halide emulsion layers. The developing agent present in the film unit develops each of the silver halide emulsion layers in the unexposed areas (since the silver halide emulsions are direct-positive ones), thus causing the developing agent to become oxidized imagewise corresponding to the unexposed areas of the direct-positive silver halide emulsion layers. The oxidized developing agent then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure*, pages 76 through 79, the disclosure of which is hereby incorporated by reference.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye-releasers are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Scavengers for oxidized developing agent can be employed in various interlayers of the photographic elements of the invention. Suitable materials are disclosed on page 83 of the November 1976 edition of *Research Disclosure*, the disclosure of which is hereby incorporated by reference.

Any material can be employed as the image-receiving layer in this invention as long as the desired function of mordanting or otherwise fixing the dye images is obtained. The particular material chosen will, of course, depend upon the dye to be mordanted. Suitable materials are disclosed on pages 80 through 82 of the November 1976 edition of *Research Disclosure*, The disclosure of which is hereby incorporated by reference.

Use of a pH-lowering material in the film units employed in this invention will usually increase the stability of the transferred image. Generally, the pH-lowering material will effect a reduction in the pH of the image layer from about 13 or 14 to at least 11 and preferably 5 to 8 within a short time after imbibition. Suitable materials and their functioning are disclosed on pages 22 and 23 of the July 1974 edition of *Research Disclosure* and pages 35 through 37 of the July 1975 edition of *Research Disclosure*, the disclosures of which are hereby incorporated by reference.

A timing or inert spacer layer can be employed in the practice of this invention over the pH-lowering layer which "times" or controls the pH reduction as a function of the rate at which alkali diffuses through the inert spacer layer. Examples of such timing layers and their functioning are disclosed in the *Research Disclosure* articles mentioned in the paragraph above concerning pH-lowering layers.

The akaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developing agent as described previously. Suitable materials and addenda frequently added to such compositions are disclosed on pages 79 and 80 of the November 1976 edition of *Research Disclosure*, the disclosure of which is hereby incorporated by reference.

While the alkaline processing composition used in this invention can be employed in a rupturable container, as described previously, to conveniently facilitate the introduction of processing composition into the film unit, other methods of inserting processing composition into the film unit could also be employed, e.g., interjecting processing solution with communicating members similar to hypodermic syringes which are attached either to a camera or camera cartridge. The processing composition may also be applied by means of a swab or by dipping in a bath, if so desired.

The alkaline solution-permeable, substantially opaque, light-reflective layer employed in certain embodiments of photographic film units used in this invention are described more fully in the November 1976 edition of *Research Disclosure*, page 82, the disclosure of which is hereby incorporated by reference.

The supports for the photographic elements used in this invention can be any material as long as it does not deleteriously affect the photographic properties of the film unit and is dimensionally stable. Typical flexible sheet materials are described on page 85 of the November 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone.

The silver halide emulsions useful in this invention, both negative-working and direct-positive ones, are well known to those skilled in the art and are described in *Product Licensing Index*, Volume 92, December 1971, publication 9232, page 107, paragraph I, "Emulsion types"; they may be chemically and spectrally sensitized as described on page 107, paragraph III, "Chemical sensitization", and pages 108 and 109, paragraph XV, "Spectral sensitization", of the above article; they can be protected against the production of fog and can be stabilized against loss of sensitivity during keeping by employing the materials described on page 107, paragraph V, "Antifoggants and stabilizers", of the above article; they can contain development modifiers, hardeners, and coating aids as described on pages 107 and 108, paragraph IV, "Development modifiers"; paragraph VII, "Hardeners"; and paragraph XII, "Coating aids", of the above article; they and other layers in the photographic elements used in this invention can contain plasticizers, vehicles and filter dyes described on page 108, paragraph XI, "Plasticizers and lubricants", and paragraph VIII, "Vehicles", and page 109, paragraph XVI, "Absorbing and filter dyes", of the above article; they and other layers in the photographic elements used in this invention may contain addenda which are incorporated by using the procedures described on page 109, paragraph XVII, "Methods of addition", of the above article; and they can be coated by using the various techniques described on page 109, paragraph XVIII, "Coating procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium, and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium in the presence of "nondiffusing" materials. "Mobile" has the same meaning.

The term "associated therewith" as used herein is intended to mean that the materials can be in either the same or different layers so long as the materials are accessible to one another.

The compounds of the present invention can generally be synthesized by one of the following methods (reference to pyridine also applies to pyrimidine):

(1) Reaction of a 2-hydrazinopyridine (or analogous heterocycle) with 1,2-naphthoquinone, and (2) Reaction of a 1-naphthol with an alkali metal 2-pyridinediazoate generated by the reaction of 2-aminopyridine and an alkyl nitrite in the presence of a strong base such as an alkali metal alkoxide.

EXAMPLE 1—PREPARATION OF COMPOUND 1

4-Amino-N-[4-(2,4-di-t-pentylphenoxy)butyl]-1-hydroxy-2-naphthamide (see U.S. Pat. No. 4,013,635, column 24) (70 g) was dissolved in dry methylene chloride (1.5 l) and 4-benzoyloxy-3-(2-pyridylazo)-1-naphthalenesulfonyl chloride (50 g) was added with stirring. An atmosphere of nitrogen was maintained throughout the reaction. Pyridine (12 g) was added to the reaction mixture and the reaction allowed to proceed overnight.

The solvent was removed and methanol added to the residue to enable it to be transferred for hydrolysis. In the meantime, a stream of nitrogen was passed through a 5 percent potassium hydroxide solution (750 ml) maintained at 60° C. on the steam bath. The methanol slurry was added to the basic solution and the hydrolysis carried out for 20 minutes. At the end of this time, the flask was cooled and the mixture acidified with hydrochloric acid. The product was filtered off and dried in the vacuum oven. After two recrystallizations from ethyl acetate, the yield was 65 g (56 percent), m.p. 195° to 196° C. $\epsilon = 1.8 \times 10^4$ in ethanol.

Intermediates:

4-Benzoyloxy-3-(2-pyridylazo)-1-naphthalenesulfonyl chloride.

4-Benzoyloxy-3-(2-pyridylazo)-1-naphthalenesulfonic acid (70 g) was added to thionyl chloride (300 ml). Dimethylformamide (30 ml) was added in portions while the reaction mixture was being stirred. After 1 hour the starting material was all in solution. The reaction mixture was poured into a large quantity of ice after a further 4 hours' stirring. The product was filtered off and dissolved in chloroform. The chloroform layer was shaken with water to destroy any remaining thionyl chloride and dried over magnesium sulfate.

Evaporation of the chloroform solution to one-quarter volume followed by cooling precipitated the sulfonyl chloride 40 g. Further concentration yielded another 15 g. Total yield 55 g, m.p. 200° to 201° C.

4-Benzoyloxy-3-(2-pyridylazo)-1-naphthalenesulfonic acid.

4-Hydroxy-3-(2-pyridylazo)-1-naphthalenesulfonic acid (110 g) was added to pyridine (350 ml) followed by benzoyl chloride (250 ml). Triethylamine (100 ml) was added slowly and the reaction mixture got warm. After 1 hour the mixture was diluted with five times its volume of acetone and filtered. The product was washed with acetone and allowed to suck dry. It was dissolved in water (minimum volume) and neutralized with hydrochloric acid. After filtration, the product was washed with acetone and ether. Yield 120 g (83 percent).

4-Hydroxy-3-(2-pyridylazo)-1-naphthalenesulfonic acid.

1,2-Naphthoquinone-4-sulfonic acid sodium salt (26 g) was dissolved in a mixture of water (500 ml) and concentrated hydrochloric acid (250 ml). To this solution was added 2-pyridylhydrazine (11 g) in water (100 ml). The reaction mixture became warm and the product started to precipitate. After 30 minutes of cooling, the product was filtered off and washed with a small volume of water, acetone and ether. Yield 32 g (96 percent).

EXAMPLE 2—PREPARATION OF COMPOUND 7

2,5-Bis[N-(3-aminophenoxycarbonyl)-N-methylaminomethyl]-3-hexadecyl-6-propylbenzoquinone (5.8 g, 8 mmol) was dissolved in 50 ml dry pyridine and treated with 3.5 g of 4-benzoyloxy-3-(2-pyridylazo)-1-naphthalenesulfonyl chloride (Example 1) in small portions. After the mixture was allowed to react for 1.5 hours, the solution was poured on ice and acidified with hydrochloric acid. The crude precipitate was slurried with 100 ml ethanol and 10 ml ammonia to remove the benzoyl group, acidified with aqueous hydrochloric acid, the solvent evaporated, the precipitate washed with aqueous acid and filtered off. It was purified by chromatography on a silica column and eluted with 2 percent ethanol in dichloromethane. 2.4 g of product was obtained having a visible spectrum $\lambda_{max}$ 480 nm, $\epsilon = 3.6 \times 10^4$.

Intermediates:

A. Preparation of 2,5-bis[N-(3-aminophenoxycarbonyl)-N-methylaminomethyl]-3-n-hexadecyl-6-n-propylquinone, I.

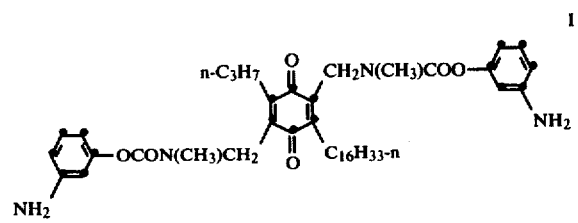

Compound II was oxidized by suspending 72 g in 1440 ml of methylene chloride and adding 180 g of PbO$_2$. The quinone dissolves as oxidation proceeds. After 1 hour, the solution is filtered, the solids washed with methylene chloride and the filtrates and washings concentrated to produce a yellow solid melting at 107° to 108.5° C.

B. Preparation of 2,5-bis[N-(3-aminophenoxycarbonyl)-N-methylaminomethyl]-3-n-hexadecyl-6-n-propylhydroquinone, II.

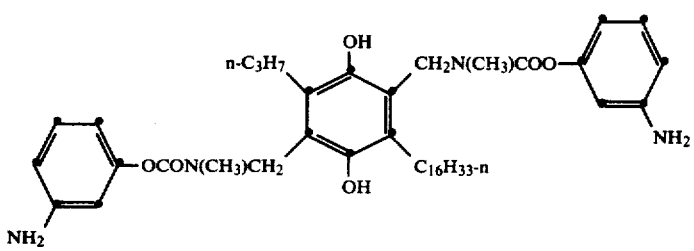

A sample of 111 g of Compound III in about 1500 ml of tetrahydrofuran was hydrogenated in the presence of 12 g of 10 percent platinum on carbon catalyst. Uptake of hydrogen was rapid and reaction was complete in about 1 hour. The mixture was filtered, the filtrate concentrated, and the residue slurried with acetonitrile. The colorless solid was collected, washed with acetonitrile, and air dried. The product melted at 190° to 192.5° C.

C. Preparation of 3-n-hexadecyl-2,5-bis[N-methyl-N-(3-nitrophenoxycarbonyl)aminomethyl]-6-n-propylhydroquinone, III.

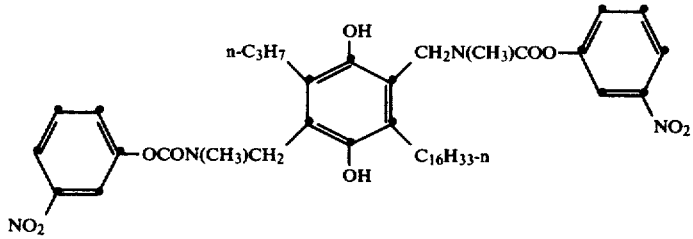

A suspension of 1 mole of Compound IV in about 7900 ml of methylene chloride was treated with 4 moles of N,N-diisopropyl-N-ethylamine, then slowly with 2 moles of a methylene chloride solution of m-nitrophenyl chloroformate. After stirring for 30 minutes, the solution was washed with a mixture of ice/2 N hydrochloric acid solution, then with water. The washed methylene chloride solution was dried over sodium sulfate and the solvent was removed by evaporation. Although the crude oil obtained is used in the next step, a sample was crystallized to produce a colorless solid melting at 89° to 95° C.

D. Preparation of 3-hexadecyl-2,5-bis(methylaminomethyl)-6-n-propylhydroquinone hydrochloride, IV.

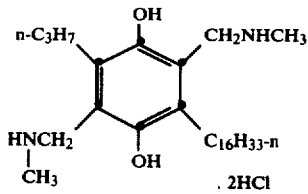

The bisoxazine, Compound VII (246 g, 0.505 mole), is refluxed for 48 hours in 2500 ml of methanol and 500 ml of concentrated hydrochloric acid.

The solution is evaporated to a solid using reduced pressure, and the light beige material is triturated with hexane and recrystallized from isopropanol.

The combined first and second crops yielded 149 g (55 percent).

E. Preparation of 5-hexadecyl-2,3,4,7,8,9-hexahydro-3,8-dimethyl-10-propylbenzo[1,2-e:4,5-e']bis[1,3]oxazine, VII.

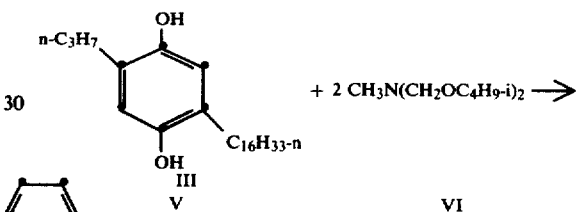

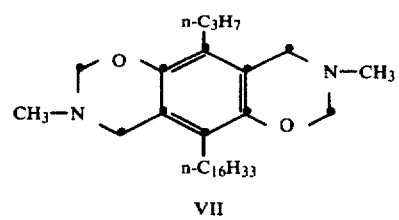

3-Hexadecyl-6-propylhydroquinone (226 g, 0.6 mole) and 250 g (1.236 moles) of N,N-(diisobutoxymethyl)methylamine are dissolved in 1500 ml of xylene and refluxed under nitrogen for 24 hours.

The xylene is concentrated off using reduced pressure and the light amber oil is poured into a beaker and allowed to solidify. The solid is broken up and washed with a small amount of cold hexane.

There is obtained 246 g of product (84 percent) which appears as one major spot on thin layer chromatography.

EXAMPLE 3—PREPARATION OF COMPOUND 11

4-Hydroxy-3-(4-hydroxy-6-methyl-2-pyrimidylazo)-1-naphthalenesulfonic acid (2.8 g, 8 mmol) was dissolved in 25 ml of pyridine with the aid of 2.5 ml triethylamine. To this solution was added the difunctional acid chloride, Compound VIII (2.4 g, 4 mmol); and the mixture was allowed to react for 3 hours. The product was precipitated with 2 l of ethyl ether. The viscous precipitate was dissolved in methanol and the solution evaporated to dryness, leaving 4.3 g of solid. That the attachment of the carrier to the dye took place at the oxygen atom on the pyridine ring was demonstrated by the formation of a nickel complex with $NiCl_2$. Visible spectrum (ethanol) $\lambda_{max}$ 470 nm, $\epsilon = 2.4 \times 10^4$.

Intermediates:

F. Preparation of 3-hexadecyl-2,5-bis(N-methylchloroformamidomethyl)-6-propylbenzoquinone, VIII.

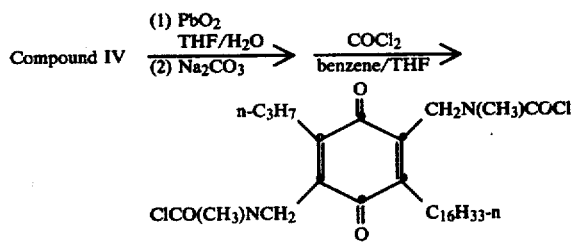

149 g of Compound IV from Example 2 are dissolved in 150 ml of tetrahydrofuran and 20 ml of water, and stirred vigorously with 12.4 g of $PbO_2$ at room temperature until presence of hydroquinone is no longer detectable by thin layer chromatography ($AgNO_3/NH_3$ test). The mixture is filtered through a medium frit glass funnel to remove $PbO_2$ and PbO, and the THF solution is stirred into a mixture of 200 ml of methylene chloride, 50 ml of water and 6 g of sodium carbonate to produce the free base. The methylene chloride phase is separated, dried over sodium sulfate, treated with 7 ml of triethylamine and added to an ice-cold solution of phosgene in 60 ml of benzene and 50 ml of tetrahydrofuran. The mixture is allowed to come to room temperature (about 1 hour), then is stirred vigorously while adding 100 g of Woelm dry column grade silicon dioxide to adsorb the amine hydrochlorides. The $SiO_2$ is removed by filtration, and solvents removed by evaporation. The product, 11.7 g of an oil which crystallizes on standing is recrystallized with about 4 to 6 parts hexane to produce an off-white solid.

EXAMPLE 4—PHOTOGRAPHIC TEST—COMPOUND 1

A single-color integral-imaging receiver element was prepared by coating successively on a polyester film support (1) a metallizing layer comprising gelatin (1.08 g/m$^2$) and nickel sulfate hexahydrate (0.58 g/m$^2$), (2) a receiving layer comprising a mixture of gelatin and poly(4-vinylpyridine), (each at 2.15 g/m$^2$), (3) a reflecting layer comprising titanium dioxide and gelatin in a 6.25/1 ratio, (4) an opaque layer of carbon dispersed in gelatin, (5) a layer comprising gelatin and a dispersion of Compound 1 (0.84 g/m$^2$), (6) a layer of a green-sensitized internal image emulsion as described in Evans, U.S. Pat. No. 3,761,276 (2.69 g/m$^2$ Ag, 2.69 g/m$^2$ gelatin), with fogging agents NA-16 and H-25 of Leone et al, U.S. Pat. No. 4,030,925, issued June 21, 1977, and 5-octadecylhydraquinone-2-sulfonic acid (16 g/mole Ag), (7) a layer of didodecylhydroquinone (1.29 g/m$^2$) dispersed in gelatin (1.61 g/m$^2$), and (8) a gelatin overcoat layer. In a comparative coating in which no metal ion is used to chelate the dye, the entire layer 1 was omitted. Layers 1 and 2 above form no part of the invention, as they are the subject of an invention by our coworkers Brust, Hamilton and Wilkes.

This integral element was exposed to a multicolor test object, then processed by spreading between it and a processing cover sheet, as described in U.S. Pat. No. 4,061,496 of Hannie et al, issued Dec. 6, 1977, at 22° C., a viscous processing composition, as described in said U.S. Pat. No. 4,061,496, by passing the transfer "sandwich" between a pair of juxtaposed rollers so that the liquid layer was about 75 μm. The dye reflection density in the unexposed areas (i.e., $D_{max}$ areas) was measured at selected intervals up to 24 hours with a recording spectrophotometer. The density at $\lambda_{max}$ after 4 minutes was determined from these plots. From the spectrophotometric curves, the final $D_{max}$, the $\lambda_{max}$ (i.e., wavelength at $D_{max}$) and "half band width" (½ BW) were determined and recorded in Table I. The "half band width" is the wavelength range at half the $D_{max}$, a measure of purity of hue: The narrower the ½ BW, the purer the hue. The light stability was determined by exposing part of the strip to a high intensity daylight (5000 footcandles) light source for two days. Values are given for the original density $D_o$, the final faded density $D_F$, and the density loss $\Delta D$.

TABLE I

| Metallization | Hue $\lambda_{max}$ (nm) | ½ BW (nm) | Light Stability $D_o$ | $D_F$ | $\Delta D$ |
|---|---|---|---|---|---|
| Ni++ | 535,575 | 115 | 1.00 | 1.00 | 0 |
| None (H) | 505 | 150 | 0.78 | 0.55 | −0.23 |

EXAMPLE 5—Photographic Test—Compound 7

A single-color photosensitive element was prepared by coating on a subbed polyester film support (g/m$^2$ in parentheses unless otherwise specified) (1) a green-sensitive 0.8 μm monodispersed silver bromide gelatin emulsion (1.1 Ag, 3.2 gelatin) and a dispersion of a mixture of (a) Compound 7 (0.51) and (b) a ballasted reducing agent precursor 4-(2-acetoxy-2-pivaloylacetamido-N-[4-(2,4-di-t-pentylphenoxy)butyl]-1-hydroxy-2-naphthamide (1.02) dissolved in diethyllauramide (1.53), and (2) an overcoat layer of gelatin (0.55). This element was exposed through a graduated density step tablet to a light source. It was then processed by spreading between it and an image receiving element at 22° C. a viscous developing composition by passing the transfer "sandwich" between a pair of juxtaposed rollers so that the liquid layer was 75 μm. The receiving element comprised a polyester film support having thereon (1) a metallizing layer comprising gelatin (1.08) and nickel sulfate hexahydrate (0.58), and (2) a receiving layer comprising a mixture of gelatin (2.15) and poly(4-vinylpyridine) (2.15). The viscous composition contained (per liter of water) 51 g potassium hydroxide, 3 g 4-hydroxymethyl-4-methyl-1-phenyl-3-pyrazolidinone, 20 g potassium bromide, 1.0 g 5-methylbenzotriazole, and 30 g carboxymethylcellulose.

After 5 minutes, the elements were peeled apart and the receiving element washed in water and dried. A transmission spectrum was obtained and normalized to a density of 1.0; $\lambda_{max}$ was 543, 570 nm.

EXAMPLE 6—Spectral Data on Dyes

Table II shows the hue, diffusion, and light stability data for dyes which have not been linked to dye-releasing carriers but which have the structural characteristics of the invention.

Dyes 30 and 31 were dissolved in 1 N potassium hydroxide. A strip of polyester film support, containing a mordant layer of gelatin and polymeric latex as above, was soaked in the alkaline solution until the dye was adsorbed to a density of 1.0 or greater and washed with water. It was then soaked in a solution of nickel (II) acetate, rinsed, soaked in an aqueous buffer solution at pH 4, washed with water and dried. The spectrophotometry was by transmission through the transparent film strip.

TABLE II
DYE UNLINKED TO CARRIER

[Structure shown]

| Dye Number | $Y^1$ | $Y^{11}$ | $R^8$ | $R^9$ | Hue $\lambda_{max}$ (nm) | ½ BW (nm) | Chelating Metal ion, Me$^{++}$ | Days | Light Stability $D_o$ | $\Delta D$ |
|---|---|---|---|---|---|---|---|---|---|---|
| 26 | 4—SO$_2$NH$_2$ | CH | H | H | 539,573 | 113 | Ni | 5 | 1.40 | −.07 |
| 27 | 4—SO$_3$H | N | H | H | 548,587 | 120 | Ni | 2 | 2.09 | −.04 |
| 28 | H | N | OH | CH$_3$ | 551 | 122 | Ni | 2 | 1.05 | −.08 |
| 29 | 4—SO$_3$H | N | OH | CH$_3$ | 543 | 119 | Ni | 2 | 1.53 | −.09 |
| 30 | 4—SO$_2$NH$_2$ | N | H | H | 545,580 | 100 | Ni | — | — | — |
| 31 | 4—SO$_2$NH$_2$ | CH | H | CH$_3$ | 535,574 | 106 | Ni | — | — | — |

Dye 26 was dissolved at a concentration of $5 \times 10^{-3}$ molar in 0.5 M sodium hydroxide solution containing hydroxyethylcellulose (Natrosol 250H, 30 g/l) as a thickener. It was spread in a thin layer between a cover sheet of polyester film support and a receiving element which consists of a polyester film support and a layer containing a mordant mixture of gelatin (2.2 g/m$^2$) and a latex, poly(styrene-co-N-benzyl-N,N-dimethyl-N-vinylbenzylammonium sulfate-co-divinylbenzene) (2.2 g/m$^2$) and containing bis(acetylacetonato)nickel (II) (0.65 g/m$^2$). The thickness of the dye layer is selected to give an optical density on the receiving element, generally around 1.5. When the dye is adsorbed to the mordant, the sheets are peeled apart, and the dyed sheet is washed and dried.

Hue: The wavelength at the maximum density ($\lambda_{max}$) of the spectrophotometric curves is recorded in the Table along with the "half band width" (½ BW).

Light Stability: The above dye-receiving elements were subjected to 5 days of a high-intensity daylight (5000 footcandles) fading test. The loss in density ($\Delta D$) was monitored spectrophotometrically.

Dyes 27, 28 and 29 were dissolved in viscous alkaline solutions as above. Each solution was imbided into an image-receiving element which comprised three layers coated on a transparent polyester film support: (1) a mordant layer, a mixture of gelatin, and the polymeric latex as above, (2) a reflecting layer of titanium dioxide (21.5 g/m$^2$) and gelatin (3.2 g/m$^2$), and (3) an opaque layer of carbon (2.7 g/m$^2$) and gelatin (1.7 g/m$^2$). This receiving element was laminated to a processing cover sheet and a viscous processing composition both as described in U.S. Pat. No. 4,061,496 referred to above. The hue and light stability data were obtained from spectrophotometric curves obtained by reading the optical density by reflection through the transparent support. The "half band width" is generally greater by reflection than by transmission.

EXAMPLE 7—Preparation of Dye 32

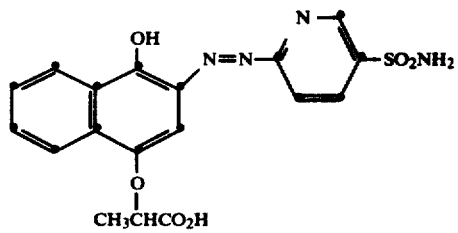

2-(5'-Sulfamoyl-2-Pyridylazo)-4-(1-Carboxyethoxy)-1-Naphthol 4-(1-Carboxyethoxy)-1,2-naphthoquinone (0.26 g, $1.06 \times 10^{-3}$ mole) and 2-hydrazino-5-sulfamoylpyridine (0.2 g, $1.06 \times 10^{-3}$ mole) were added to acetic acid (5 ml), along with 2 to 3 drops of concentrated hydrochloric acid. After stirring for 3 hours, at room temperature, the mixture was filtered to remove traces of solid. The filtrate was poured into distilled water (30 ml) and filtered again. The precipitate was washed with water and air dried; yield 0.26 g (59 percent).

Intermediates:

2-Chloro-5-Chlorosulfonylpyridine

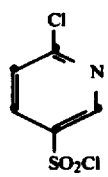

5-Amino-2-chloropyridine (10.0 g, 0.078 mole) was added to concentrated hydrochloric acid (160 ml), and the solution was cooled to −8° C. (CH₃OH/ice bath). A solution of sodium nitrite (5.37 g, 0.078 mole) in water (20 ml) was added below the solution surface at a rate to maintain the temperature below −5° C.

Cupric chloride dihydrate (4.4 g) was added to acetic acid (160 ml) saturated with sulfur dioxide at 3° C.

The diazonium salt solution described above was added to the SO₂ mixture. After stirring for 15 minutes at 0° C. and 30 minutes at room temperature, the reaction mixture was poured into ice/water (500 ml). The precipitate was collected by filtration and dried in vacuo at room temperature over calcium sulfate. The purple solid (8.8 g) was dissolved in tetrahydrofuran (200 ml), slurried with carbon and filtered. The filtrate was concentrated to an oil which crystallized to a white solid; yield 8.12 g (49 percent), m.p. 46° to 48° C.

2-Chloro-5-Sulfamoylpyridine

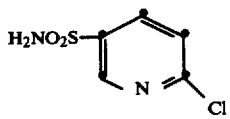

2-Chloro-5-chlorosulfonylpyridine (2.84 g, 0.0134 mole) was added to concentrated ammonium hydroxide (50 ml) and the mixture was boiled. After adding more concentrated ammonium hydroxide (50 ml), and extending boiling until the reaction volume was approximately 50 ml, the reaction mixture was cooled in an ice bath to cause precipitation of the product. The solid was collected by filtration, washed with water and air dried; yield, 2.17 g (84 percent), m.p. 153° to 155° C. A melting point of 155° to 156° C. was observed after recrystallization from water.

2-Hydrazino-5-Sulfamoylpyridine

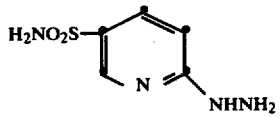

2-Chloro-5-sulfamoylpyridine (1.0 g, 0.005 mole) was added to methanol (20 ml) and the reaction mixture was cooled to 5° C. before adding hydrazine hydrate (0.50 ml, 0.52 g, 0.01 mole). After stirring for 10 minutes at 5° C., the mixture was refluxed for 45 minutes. Additional hydrazine hydrate (1.0 ml) was added and the mixture was refluxed for approximately 12 hours. The reaction mixture was concentrated in vacuo to an oil which was slurried with 40 ml of boiling ethanol. The ethanol layer was collected by decantation and cooled in an ice bath to produce a white solid which was collected by filtration and air dried; yield, 0.69 g (73 percent).

4-(1-Carboxyethoxy)-1,2-Naphthoquinone

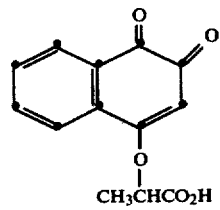

To a solution of 38.0 g potassium dihydrogen phosphate in 7.5 liters of distilled water (pH 4.0) was added 89.4 g (0.33 mole) of potassium nitrosodisulfonate (Fremy's reagent). To this solution was added immediately a solution of 34.8 g (0.15 mole) of 2-(4-hydroxy-1-naphthoxy)propionic acid in 125 ml ethanol. The mixture was stirred for 2.5 hours under nitrogen at room temperature. The yellow-brown solid was collected, washed with a little water and dried (under nitrogen). The yield was 30.0 g (81 percent). The crude product melted at 182° to 184° C.

EXAMPLE 8—Photographic Test—Dye 32

A receiving element was prepared by coating on a poly(ethylene terephthalate) film support (1) a metallizing layer comprising gelatin (1.08 g/m²) and nickel sulfate hexahydrate (0.58 g/m²), and (2) a receiving layer comprising a mixture of gelatin and poly(4-vinylpyridine) (each at 2.15 g/m²).

The receiving element was immersed in an alkaline solution of dye 32. The receiver was removed from the dye solution, washed in distilled water, placed in a pH 6.5 buffer solution and dried. A transmission spectra was obtained and normalized to a density of 1.0. The $\lambda_{max}$ was 637 nm, and the half band width (½ BW) was 130 nm.

EXAMPLE 9—PREPARATION OF DYE 33

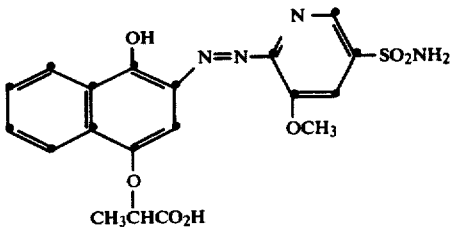

2-(3'-Methoxy-5'-Sulfamoyl-2-Pyridylazo)-4-(1-Carboxyethoxy)-1-Naphthol 4-(1-Carboxyethoxy)-1,2-naphthoquinone (0.22 g, 9×10⁻⁴) and 2-hydrazino-3-methoxy-5-sulfamoylpyridine (0.2 g, 9×10⁻⁴ mole) were added to acetic acid (15 ml), along with 2 to 3 drops of concentrated hydrochloric acid. After stirring overnight, the resulting precipitate was collected by filtration, air dried, slurried twice with boiling acetic acid (5 ml) and isolated again by filtration; yield, 80 mg (20 percent).

Intermediates:

4-(1-Carboxyethoxy)-1,2-Naphthoquinone

See Example 7 above.

3-Methoxy-5-Nitro-2-Pyridone

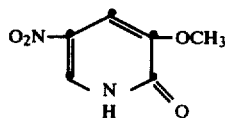

Sodium hydroxide (8.6 g, 0.215 mole) and 2,3-dihydroxypyridine (22.0 g, 0.20 mole) were added to distilled water (75 ml). After cooling to 5° C., dimethylsulfate (25.0 g, 0.21 mole) was added dropwise; the reaction mixture was stirred for 20 hours while slowly warming to room temperature. The water was removed in vacuo (approximately 65° C.) to obtain a syrup which was dissolved in concentrated sulfuric acid (50 to 60 ml) at 5° C. A cold mixture of concentrated nitric acid (20 ml) in concentrated sulfuric acid (20 ml) was added at a rate to maintain the reaction mixture between 10° to 15° C. After the addition was complete, the mixture was stirred for 30 minutes at 5° C. and then poured onto ice (approximately 400 ml). The resulting red precipitate was collected by filtration and recrystallized from water; yield, 5.8 g (17 percent).

2-Chloro-3-Methoxy-5-Nitropyridine

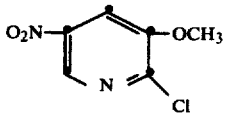

3-Methoxy-5-nitro-2-pyridone (5.7 g, 0.034 mole) was added to a combination of phosphorus pentachloride (5.0 g) and phosphorus oxychloride (40 ml); the reaction mixture was refluxed for 2.5 hours, cooled, poured over ice/water (300 ml) and stirred for 30 minutes. The resulting solid was collected by filtration, washed with water and air dried; yield, 1.72 g (27 percent), m.p. 40° to 41° C.

5-Amino-2-Chloro-3-Methoxypyridine

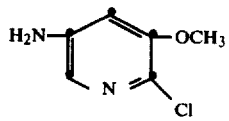

2-Chloro-3-methoxy-5-nitropyridine (1.5 g, 0.008 mole) was added to concentrated hydrochloric acid (15 ml) at 5° C., followed by stannous chloride (5.0 g). The reaction mixture was stirred for 10 minutes at 5° C., heated for 30 minutes on a steam bath, cooled, neutralized with aqueous sodium hydroxide (20 percent by weight) and extracted with 1,1,1-trichloroethane. The trichloroethane extract was dried over MgSO$_4$ and evaporated in vacuo to yield a white solid; yield, 1.02 g (91 percent), m.p. 93° to 94° C.

2-Chloro-5-Chlorosulfonyl-3-Methoxypyridine

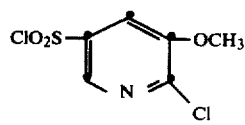

5-Amino-2-chloro-3-methoxypyridine (0.75 g, 4.7×10$^{-3}$ mole) was added to concentrated hydrochloric acid (20 ml) at −8° C., followed by slow addition of sodium nitrite (0.33 g) in water (5 ml) below the surface of the reaction mixture.

Cupric chloride dihydrate (0.3 g) was added to acetic acid (20 ml) saturated with sulfur dioxide at 5° C., followed by rapid addition of the above-described diazonium solution. The reaction mixture was stirred in an ice bath for 10 minutes, then at room temperature for 30 minutes and poured over ice/H$_2$O (approximately 200 ml) which caused the formation of an oil. The oil was extracted with ethyl acetate. The extract was dried over MgSO$_4$ and evaporated in vacuo to yield an oil which was used directly for the next intermediate.

2-Chloro-3-Methoxy-5-Sulfamoylpyridine

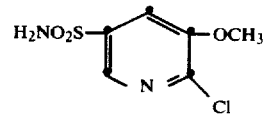

The above-described oil was added to concentrated ammonium hydroxide (10 ml). After heating the mixture to the boiling point, an additional 10 ml of concentrated ammonium hydroxide was added. The reaction mixture was concentrated to approximately 10 ml by boiling and cooled in an ice bath. The resulting precipitate was collected by filtration, washed with distilled water and air dried; yield, 0.45 g (43 percent), m.p. 156° to 158° C.

2-Hydrazino-3-Methoxy-5-Sulfamoylpyridine

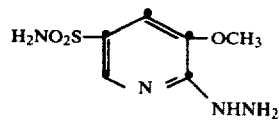

2-Chloro-3-methoxy-5-sulfamoylpyridine (0.3 g, 1.35×10$^{-3}$ mole) and hydrazine hydrate (0.53 g, approximately 0.01 mole) were added to methanol (20 ml). After refluxing overnight, the reaction mixture was stripped of methanol in vacuo to yield an oil which was cooled in an ice bath and triturated with water (5 ml). The precipitate was collected by filtration and air dried; yield, 0.22 g (75 percent).

EXAMPLE 10—PHOTOGRAPHIC TEST—DYE 33

Dye 33 was mordanted and metallized as described in Example 8. Samples of the receiving element were buffered at pH 4.65 and 7.0 and subjected to a high-intensity daylight (5000 foot-candles) fading test. The percent dye density, measured spectrophotometrically, remaining after 2 days was 94 percent and after 10 days was 90 percent. A transmission spectrum was obtained and normalized to a density of 1.0. The $\lambda_{max}$ was 661 nm.

EXAMPLE 11—PREPARATION OF COMPOUND 16

Dye 33 (2.08 g, $2.6 \times 10^{-3}$ mole), prepared as described in Example 9, N-ethoxycarbonyl-2-ethoxy-1,2-dihdroquinoline (3.25 g, 0.013 mole) and 2,5-Bis{[N-(3-aminophenoxycarbonyl)-N-methylamino]methyl}-3,6-didodecylbenzoquinone (2.08 g, $2.6 \times 10^{-3}$ mole) were added to dimethylformamide (50 ml, stored over molecular sieves) under nitrogen gas. After stirring for 90 minutes under nitrogen at room temperature and heating for 15 minutes on a steam bath, the reaction mixture was cooled and poured into dilute hydrochloric acid (800 ml). The precipitate was collected by filtration, slurried with water (200 ml), filtered and air dried; yield, 4.28 g (99 percent crude). The crude product was purified by column chromatography on silica gel, eluted with acetic acid (2 percent)/dichloromethane, followed by 2 percent acetic acid/20 percent ethyl acetate in dichloromethane.

EXAMPLE 12—PREPARATION OF DYE 34

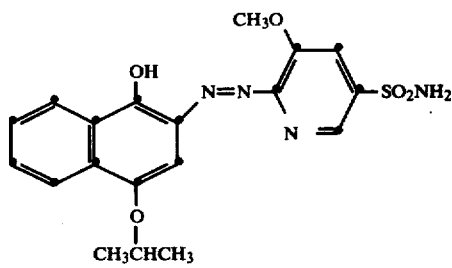

2-(3'-Methoxy-5'-Sulfamoyl-2-Pyridylazo)-4-Isopropoxy-1-Naphthol

A mixture of 2-hydrazino-3-methoxy-5-sulfamoyl-pyridine (0.25 g, $1.15 \times 10^{-3}$ mole) prepared as described in Example 9, 4-isoproxy-1,2-naphthoquinone (0.26 g, $1.2 \times 10^{-3}$ mole) and acetic acid (10 ml) was stirred for 1 hour, filtered, washed with acetic acid and water, and air dried; yield, 0.36 g. The crude product was extracted with ethanol; the extract upon chilling yielded a solid; yield, 0.19 g (40 percent), m.p. 289° C.

EXAMPLE 13—PHOTOGRAPHIC TEST—DYE 34

Dye 34 was tested for light stability in the same manner as described in Example 10. The results were as follows:

| pH | 2 Days | 10 Days |
|---|---|---|
| 4.65 | 97 percent | 92 percent |
| 7.0 | 98 percent | 95 percent |

A transmission spectrum was obtained and normalized to a density of 1.0. The $\lambda_{max}$ was 650 nm.

EXAMPLE 13—PREPARATION OF COMPOUND 17

A mixture of 4-(1-carboxyethoxy)-1,2-naphthoquinone (0.11 g, $4.9 \times 10^{-4}$ mole), 4-(2-hydrazino-3-methoxy-5-pyridylsulfonamido)-N,N-dioctadecyl-1-hydroxy-2-naphthamide (0.80 g, $8.76 \times 10^{-4}$ mole) and acetic acid (10 ml) was stirred for 18 hours, filtered, washed with acetic acid, water and air dried; yield, 0.30 g. A portion of the crude product (0.25 g) was stirred in dichloromethane and collected again by filtration; yield, 0.15 g (31 percent), m.p. 145° C.

Intermediates:

4-(1-Carboxyethoxy)-1,2-naphthoquinone

See Example 7 above.

4-(2-Chloro-3-Methoxy-5-Pyridylsulfonamido)-N,N-Dioctadecyl-1-Hydroxy-2-Naphthamide

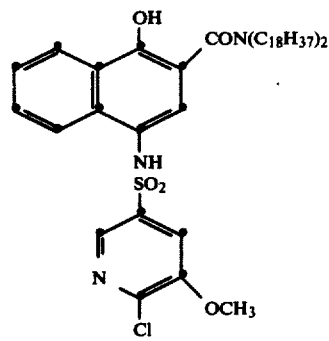

A mixture of 2-chloro-5-chlorosulfonyl-3-methoxypyridine (0.65 g, $2.68 \times 10^{-3}$ mole) (see Example 9), 4-amino-N,N-dioctadecyl-1-hydroxy-2-naphthamide (1.40 g, $1.98 \times 10^{-3}$ mole) and pyridine (0.20 g, $2.5 \times 10^{-3}$ mole) was stirred overnight at room temperature. Additional pyridine (7 drops) was employed after the first 2½ hours of stirring. The reaction mixture was concentrated in vacuo and diluted with water to precipitate an oil which changed to a waxy solid upon trituration with water. The waxy solid was dissolved in toluene and purified by column chromatography on silica gel using toluene. The toluene fraction was concentrated to a solid which was recrystallized from ethanol; yield, 0.40 g (22 percent), m.p. 85° to 87° C.

4-(2-Hydrazino-3-Methoxy-5-Pyridylsulfonamido)-N,N-Dioctadecyl-1-Hydroxy-2-Naphthamide

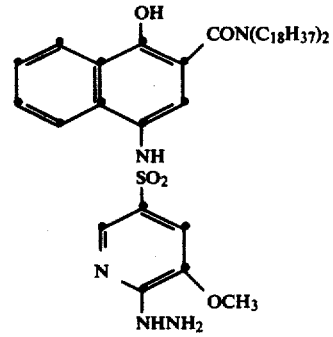

A mixture of 4-(2-chloro-3-methoxy-5-pyridylsulfonamido)-N,N-dioctadecyl-1-hydroxy-2-naphthamide (0.80 g, $8.76 \times 10^{-4}$ mole), hydrazine hydrate (95 percent, 0.1 g, $3 \times 10^{-4}$ mole) and methanol (25 ml) was heated for 17 hours on a steam bath. The reaction mixture was filtered hot to yield 0.62 g precipitate which was dissolved in toluene and chromatographed on silica gel. Toluene removed the impurities and the product was obtained with toluene/dichloromethane (1:1) and then pure dichloromethane. These fractions were concentrated to an oil which was dissolved in ethanol and cooled to yield a solid; yield, 0.38 g (48 percent), m.p. 99° to 101° C.

EXAMPLE 14—PREPARATION OF COMPOUND 18

A mixture of 4-isoproxy-1,2-naphthoquinone (0.60 g, $2.8 \times 10^{-3}$ mole), 4-(2-hydrazino-3-methoxy-5-pyridyl-sulfonamido)-N,N-dioctadecyl-1-hydroxy-2-naphthamide (Example 13, 2.0 g, $2.2 \times 10^{-3}$) and acetic acid (53 ml) was stirred for 15.5 hours at room temperature. A solid was filtered off, washed with water and air dried. The solid was recrystallized with difficulty from ligroin; yield, 0.50 g (21 percent), m.p. 108° to 110° C.

EXAMPLE 15

Tables III through VII show absorption maxima for dyes which have not been linked to dye-releasing carriers, but which have the structural characteristics of the invention. The dyes in Tables III and VII were mordanted and metallized as in Example 8. The dyes in Tables IV, V and VI were dissolved in a 1:1 dioxane/water solution containing nickel ions. The following absorption maxima of the dyes in solution were obtained:

TABLE III

| Dye Number | $R^{10}$ | $R^{11}$ | $R^{12}$ | $R^{13}$ | $R^{14}$ | $\lambda_{max}$ (nm) |
|---|---|---|---|---|---|---|
| 35 | —CHCH$_3$ \| CO$_2$H | H | H | H | H | 610* |
| 36 | —CHCH$_3$ \| CO$_2$H | H | SO$_2$NH$_2$ | H | CH$_3$ | 645 |
| 37 | —CHCH$_3$ \| CO$_2$H | H | CONH$_2$ | H | H | 634 |
| 38 | —CHCH$_3$ \| CO$_2$H | H | CN | H | H | 641 |
| 39 | —CHCH$_3$ \| CO$_2$H | H | SO$_2$NHCH$_3$ | H | OCH$_3$ | 660 |
| 40 | —CHCH$_3$ \| CO$_2$H | H | SO$_2$NHC(CH$_3$)$_3$ | H | OCH$_3$ | 661 |
| 41 | —CHCONH—(C$_6$H$_4$)—SO$_2$NH$_2$ \| CH$_3$ | H | SO$_2$NH$_2$ | H | OCH$_3$ | 650 |
| 42 | —CHCONH(CH$_2$)$_3$SO$_2$NH$_2$ \| CH$_3$ | H | SO$_2$NH$_2$ | H | OCH$_3$ | 651 |
| 43 | —CHCH$_3$ \| CO$_2$H | H | SO$_2$NH—(C$_6$H$_4$)—OH | H | OCH$_3$ | 664 |
| 44 | CH$_3$ | H | SO$_2$NH—(C$_6$H$_4$)—OH | H | OCH$_3$ | 655 |
| 45 | —CH(CH$_3$)$_2$ | H | SO$_2$NH—(C$_6$H$_4$)—OH | H | OCH$_3$ | 665 |

TABLE III-continued

[Structure: Naphthalene with OH, OR¹⁰, and N=N linked to pyridine ring bearing R¹¹, R¹², R¹³, R¹⁴]

| Dye Number | R¹⁰ | R¹¹ | R¹² | R¹³ | R¹⁴ | $\lambda_{max}$ (nm) |
|---|---|---|---|---|---|---|
| 46 | —CHCH₃ \| CO₂H | H | —SO₂NH—C₆H₄—SO₂NH₂ | H | OCH₃ | — |
| 47 | —CH(CH₃)₂ | H | —SO₂NH—C₆H₄—SO₂NH₂ | H | OCH₃ | 652* |
| 48 | —CHCH₃ \| CO₂t-butyl | H | —SO₂NH—C₆H₄—SO₂NH₂ | H | OCH₃ | 645* |
| 49 | —CHCH₃ \| CO₂H | H | H | H | SO₂NH₂ | 625 |
| 50 | —CHCH₃ \| CO₂H | H | NHSO₂CH₃ | H | H | 625* |
| 51 | —CHCH₃ \| CO₂H | H | SO₂NH₂ | H | Cl | 641 |
| 52 | —CHCH₃ \| CO₂H | H | NH₂ | H | H | 630* |
| 53 | —CHCH₃ \| CO₂H | H | H | H | OCH₃ | 632* |
| 54 | —CHCH₃ \| CO₂H | H | SO₂NH₂ | H | SO₂NH₂ | 626 |
| 55 | CH(CH₃)₂ | Cl | H | CO₂H | H | 626* |
| 56 | CH(CH₃)₂ | Cl | H | CONH₂ | H | 637* |
| 57 | CH(CH₃)₂ | H | H | CO₂H | H | — |
| 58 | CH(CH₃)₂ | H | H | CONH₂ | H | 625* |
| 59 | —CHCH₃ \| CO₂H | H | SO₂CH₃ | H | H | 634 |
| 60 | —CHCH₃ \| CO₂H | H | CN | H | Cl | 644 |
| 61 | —CHCH₃ \| CO₂H | H | CO₂H | H | Cl | 639 |

*$\lambda_{max}$ (1:1 Dioxane/H₂O + Ni⁺⁺)

TABLE IV

Structure: 1-hydroxy-4-OR15-naphthalene with 2-azo linkage to pyrimidine bearing R16, R17, R18

| Dye Number | R15 | R16 | R17 | R18 | λmax (nm) |
|---|---|---|---|---|---|
| 62 | —CHCH₃—CO₂H | H | H | H | 590 |
| 63 | —CHCH₃—CO₂H | H | H | OCH₃ | 617 |
| 64 | —CHCH₃—CO₂H | H | Cl | H | 585 |

TABLE V

Structure: 1-hydroxy-4-OR19-naphthalene with 2-azo linkage to pyrazine bearing R20, R21, R22

| Dye Number | R19 | R20 | R21 | R22 | λmax (nm) |
|---|---|---|---|---|---|
| 65 | —CHCH₃—CO₂H | H | H | H | 626 |
| 66 | —CHCH₃—CO₂H | H | H | Cl | 628 |
| 67 | —CHCH₃—CO₂H | H | H | OCH₃ | 646 |

TABLE VI

Structure: 1-hydroxy-4-R23-naphthalene (with R24 substituent) with 2-azo linkage to R25

| Dye Number | R23 | R24 | R25 | λmax (nm) |
|---|---|---|---|---|
| 68 | —OCHCH₃—CO₂H | H | quinolin-2-yl | 640 |
| 69 | CH₃ | H | pyrazin-2-yl | 581/615 |
| 70 | CH₃ | H | pyrimidin-4-yl | 560 |
| 71 | CH₃ | H | 5-methoxypyrimidin-4-yl | 611 |
| 72 | CH₃ | H | 3-methyl-1,2,4-thiadiazol-5-yl | — |
| 73 | CH₃ | H | pyridazin-3-yl | — |
| 74 | CH₃ | H | 3-amino-1,2,4-triazol-5-yl | — |
| 75 | H | 8-NHSO₂CH₃ | benzothiazol-2-yl | 665 |
| 76 | CH₃ | H | 3-methoxy-5-sulfamoylpyridin-2-yl | 635 |

TABLE VI-continued
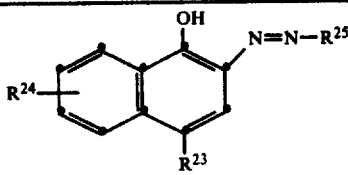
| Dye Number | R²³ | R²⁴ | R²⁵ | λ$_{max}$ (nm) |
|---|---|---|---|---|
| 77 | CH₃ | H | 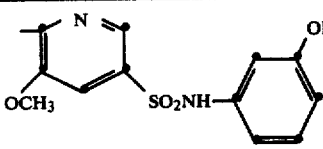 | 630 |
| 78 | CH₃ | H | 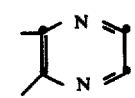 | 590/620 |
| 79 | CH₃ | H | 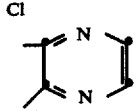 | 633 |
| 80 | —OCHCH₃<br>    \|<br>    CO₂H | H | 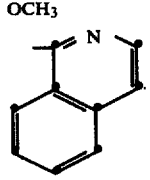 | 648 |
| 81 | CH₃ | H | 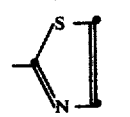 | — |
| 82 | —OCHCH₃<br>    \|<br>    CO₂H | H | 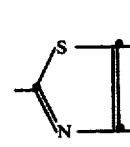 | — |
TABLE VII
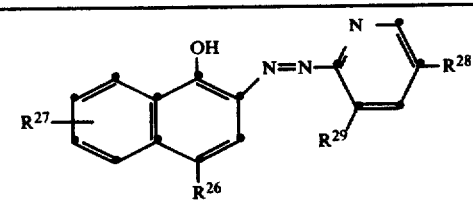
| Dye Number | R²⁶ | R²⁷ | R²⁸ | R²⁹ | λ$_{max}$ (nm) |
|---|---|---|---|---|---|
| 83 | H | 8-NHSO₂——OH | H | H | 598* |
| 84 | H | 8-NHSO₂—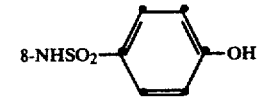—OH | —NHSO₂CH₃ | H | 612* |
| 85 | H | 8-NHSO₂CH₃ | —NHSO₂CH₃ | H | 608* |
| 86 | OCH₃ | 8-NHSO₂——OH | —SO₂NH₂ | H | 654 |

TABLE VII-continued

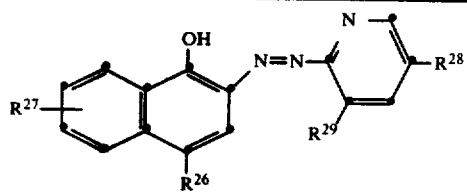

| Dye Number | R²⁶ | R²⁷ | R²⁸ | R²⁹ | λ_max (nm) |
|---|---|---|---|---|---|
| 87 | H | 8-NHSO$_2$CH$_3$ | —SO$_2$NH—C$_6$H$_4$—OH | OCH$_3$ | 649 |
| 88 | H | 8-NHSO$_2$CH$_3$ | —SO$_2$NH$_2$ | OCH$_3$ | 648 |
| 89 | OCH$_3$ | 8-NHSO$_2$CH$_3$ | —SO$_2$NH$_2$ | OCH$_3$ | 674 |
| 90 | H | { 8-NHSO$_2$CH$_3$, 6-SO$_2$NH$_2$ } | —SO$_2$NH$_2$ | OCH$_3$ | 650 |
| 91 | H | { 8-NHSO$_2$CH$_3$, 6-SO$_2$NH$_2$ } | —SO$_2$NH—C$_6$H$_4$—OH | OCH$_3$ | 651 |
| 92 | OCH$_3$ | 8-NHSO$_2$CH$_3$ | —SO$_2$NH—C$_6$H$_4$—OH | OCH$_3$ | 676 |
| 93 | H | { 8-NHSO$_2$CH$_3$, 6-SO$_2$NH$_2$ } | —SO$_2$NH$_2$ | H | 623 |
| 94 | H | 6-SO$_2$NH$_2$ | —SO$_2$NH$_2$ | OCH$_3$ | 639 |
| 95 | H | 7-OCH$_3$ | —SO$_2$NH$_2$ | OCH$_3$ | 648 |
| 96 | OCH$_3$ | 6-SO$_2$NH$_2$ | —SO$_2$NH$_2$ | OCH$_3$ | 669 |
| 97 | OCH$_3$ | { 8-NHSO$_2$CH$_3$, 6-SO$_2$NH$_2$ } | —SO$_2$NH$_2$ | OCH$_3$ | 676 |
| 98 | OCH$_3$ | { 8-NHSO$_2$CH$_3$, 6-SO$_2$NH$_2$ } | —SO$_2$NH$_2$ | Cl | 668 |
| 99 | OCH$_3$ | { 8-NHSO$_2$CH$_3$, 6-SO$_2$NH$_2$ } | —SO$_2$NH—C$_6$H$_4$—OH | OCH$_3$ | 683 |
| 100 | OCH$_3$ | 8-NHSO$_2$CH$_3$ | —SO$_2$NH—C$_6$H$_3$(SO$_2$NH$_2$)—OH | OCH$_3$ | 667* |
| 101 | H | 6-SO$_2$NH$_2$ | —SO$_2$NH—C$_6$H$_4$—OH | OCH$_3$ | 670 |

*λ_max (3:1 Dioxane/H$_2$O + Ni$^{++}$)

The invention has been described in detail with particular reference to preferred embodiments thereof, but it will be appreciated that variations and modifications can be effected within the spirit and scope of the invention.

What is claimed is:

1. A photographic element comprising a support having thereon at least one photosensitive silver halide emulsion layer, said emulsion layer having associated therewith a nondiffusible compound having at least one releasable 2-(2-heterocyclylazo)-1-naphthol dye moiety, said compound containing a ballasted carrier moiety which is capable of releasing said diffusible azo dye as a function of development of said silver halide emulsion layer under alkaline conditions, said heterocyclyl moiety containing a nitrogen atom adjacent to the point of attachment to the azo linkage, said heterocyclyl moiety not being substituted with a nitro group, and said heterocyclyl moiety being selected from the group consisting of pyridine, pyrimidine, quinoline, isoquinoline, pyrazine, pyridazine, thiazole, thiadiazole, triazole, benzothiazole and acinaphthothiazole.

2. The photographic element of claim 1 wherein said compound has the formula:

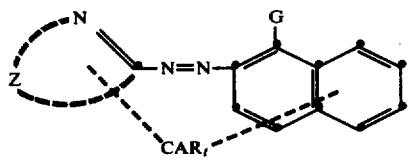

wherein:
G is a hydroxy group, a salt thereof, or a hydrolyzable precursor thereof; or a group which together with

is CAR, said CAR being bonded to the naphthalene group through the oxygen of said

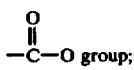 group;

Z represents the atoms necessary to complete said heterocyclyl moiety;
CAR represents said ballasted carrier moiety; and
t is a positive integer of 1 to 2.

3. The photographic element of claim 2 wherein t is 1, G is OH and Z represents the atoms necessary to complete a pyridine or pyrimidine ring.

4. The photographic element of claim 2 wherein G is hydroxy; or an acyloxy group having the formula —O—COR$^1$, —OCOOR$^1$, or —OCON(R$^1$)$_2$, wherein R$^1$ is an alkyl group having 1 to about 8 carbon atoms or an aryl group having 6 to about 12 carbon atoms, or a group which together with

is CAR, said CAR group being bonded to the naphthalene group through the oxygen of said

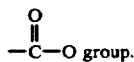 group.

5. The photographic element of claim 2 wherein CAR is a group having the formula:

(Ballast-Carrier-Link)— wherein:
(a) Ballast is an organic ballasting radical of such molecular size and configuration as to render said compound nondiffusible in said photographic element during development in an alkaline processing composition;
(b) Carrier is an oxidizable acyclic, carbocyclic or heterocyclic moiety; and
(c) Link represents a group which upon oxidation of said carrier moiety is capable of being hydrolytically cleaved to release said diffusible azo dye.

6. The photographic element of claim 5 wherein the Carrier moiety contains atoms according to the following configuration:

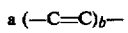

wherein:
b is a positive integer of 1 to 2; and
a represents the radicals OH, SH, NH—, or hydrolyzable precursors thereof.

7. The photographic element of claim 2 wherein CAR is a group having the formula:

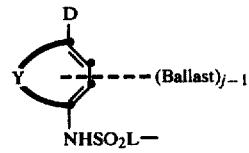

wherein:
(a) Ballast is an organic ballasting radical of such molecular size and configuration as to render said compound nondiffusible in said photographic element during development in an alkaline processing composition;
(b) D is OR$^2$ or NHR$^3$ wherein R$^2$ is hydrogen or a hydrolyzable moiety and R$^3$ is hydrogen or a substituted or unsubstituted alkyl group of 1 to 22 carbon atoms;
(c) Y represents the atoms necessary to complete a benzene nucleus, a naphthalene nucleus, or a 5 to 7 membered heterocyclic ring;
(d) j is a positive integer of 1 to 2 and is 2 when D is OR$^2$ or when R$^3$ is hydrogen or an alkyl group of less than 8 carbon atoms; and
(e) L is a linking group which is [X—(NR$^4$—J)$_q$]$_m$— or X—J—NR$^4$— wherein:
 (i) X represents a bivalent linking group of the formula —R$^5$—L′$_n$—R$^5$p— where each R$^5$ can be the same or different and each represents an alkylene radical having 1 to about 8 carbon atoms; a phenylene radical; or a substituted phenylene radical having 6 to about 9 carbon atoms;
 (ii) L′ represents a bivalent radical selected from oxy, carbonyl, carboxamido, carbamoyl, sulfonamido, ureylene, sulfamoyl, sulfinyl or sulfonyl;
 (iii) n is an integer of 0 or 1;
 (iv) p is 1 when n equals 1 and p is 1 or 0 when n equals 0, provided that when p is 1 the carbon content of the sum of both R$^5$ radicals does not exceed 14 carbon atoms;
 (v) R$^4$ represents a hydrogen atom, or an alkyl radical having 1 to about 6 carbon atoms;
 (vi) J represents a bivalent radical selected from sulfonyl or carbonyl;
 (vii) q represents an integer of 0 or 1; and
 (viii) m represents an integer of 0, 1 or 2.

8. The photographic element of claim 7 wherein D is OH, j is 2, Y is a naphthalene nucleus, G is OH, and t is 1.

9. The photographic element of claim 1 wherein said diffusible azo dye is released as an inverse function of said development of said silver halide emulsion layer under alkaline conditions.

10. The photographic element of claim 9 wherein said ballasted carrier moiety is a group having the formula:

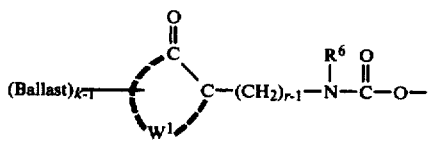

wherein:

Ballast is an organic ballasting radical of such molecular size and configuration as to render said compound nondiffusible in said photographic element during development in an alkaline processing composition;

$W^1$ represents at least the atoms necessary to complete a quinone nucleus;

r is a positive integer of 1 or 2;

$R^6$ is an alkyl radical having 1 to about 40 carbon atoms or an aryl radical having 6 to about 40 carbon atoms; and k is a positive integer of 1 to 2 and is 2 when $R^6$ is a radical of less than 8 carbon atoms.

11. The photographic element of claim 9 wherein said ballasted carrier moiety is a group having the formula:

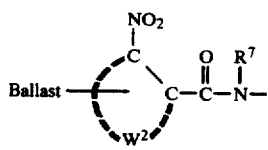

wherein:

Ballast is an organic ballasting radical of such molecular size and configuration as to render said compound nondiffusible in said photographic element during development in an alkaline processing composition;

$W^2$ represents at least the atoms necessary to complete a benzene nucleus; and $R^7$ is an alkyl radical having 1 to about 4 carbon atoms.

12. The photographic element of claim 9 wherein said ballasted carrier moiety is a group having the formula:

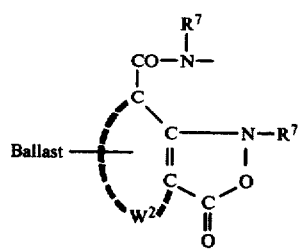

wherein:

Ballast is an organic ballasting radical of such molecular size and configuration as to render said compound nondiffusible in said photographic element during development in an alkaline processing composition;

$W^2$ represents at least the atoms necessary to complete a benzene nucleus; and $R^7$ is an alkyl radical having 1 to about 4 carbon atoms.

13. The photographic element of claim 9 wherein said ballasted carrier moiety is a group having the formula:

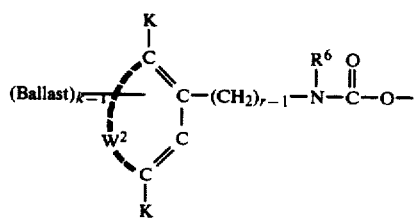

wherein:

Ballast is an organic ballasting radical of such molecular size and configuration as to render said compound nondiffusible in said photographic element during development in an alkaline processing composition;

$W^2$ represents at least the atoms necessary to complete a benzene nucleus;

r is a positive integer of 1 or 2;

$R^6$ is an alkyl radical having 1 to about 40 carbon atoms or an aryl radical having 6 to about 40 carbon atoms;

k is a positive integer of 1 to 2 and is 2 when $R^6$ is a radical of less than 8 carbon atoms; and K is OH or a hydrolyzable precursor thereof.

14. The photographic element of claim 1 wherein said dye-releasing compound is:

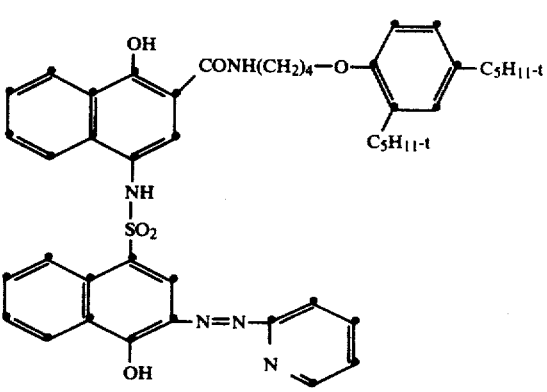

15. The photographic element of claim 1 wherein said dye-releasing compound is:

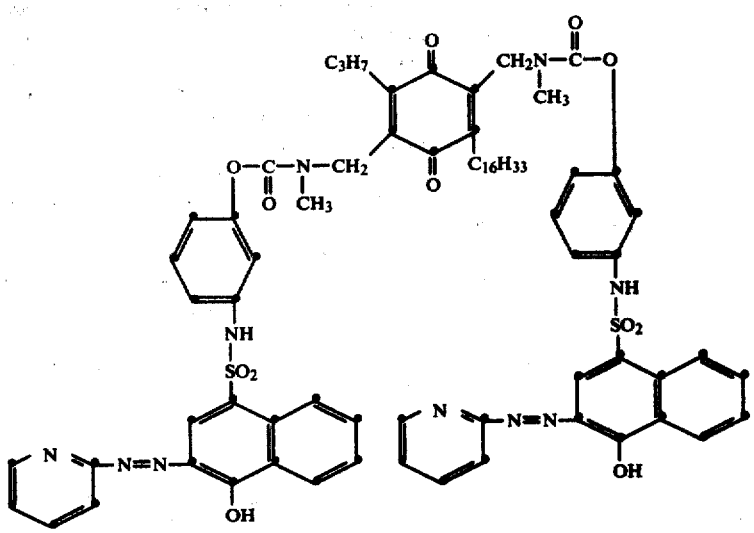

16. In a photographic assemblage comprising:
 (a) a support having thereon at least one photosensitive silver halide emulsion layer having associated therewith a dye image-providing material;
 (b) a dye image-receiving layer; and
 (c) an alkaline processing composition and means for discharging same within said assemblage;
said assemblage containing a silver halide developing agent, the improvement wherein said dye image-providing material is a nondiffusible compound having at least one releasable 2-(2-heterocyclylazo)-1-naphthol dye moiety, said compound containing a ballasted carrier moiety which is capable of releasing said diffusible azo dye as a function of development of said silver halide emulsion layer under alkaline conditions, said heterocyclyl moiety containing a nitrogen atom adjacent to the point of attachment to the azo linkage, said heterocyclyl moiety not being substituted with a nitro group, and said heterocyclyl moiety being selected from the group consisting of pyridine, pyrimidine, quinoline, isoquinoline, pyrazine, pyridazine, thiazole, thiadiazole, triazole, benzothiazole and acinaphthothiazole.

17. The photographic assemblage of claim 16 wherein said compound has the formula:

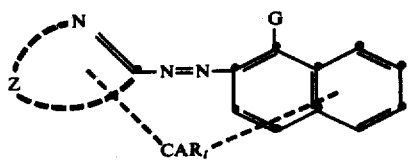

wherein:
G is a hydroxy group, a salt thereof, or a hydrolyzable precursor thereof; or a group which together with

is CAR, said CAR being bonded to the naphthalene group through the oxygen of said

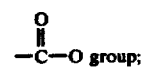

Z represents the atoms necessary to complete said heterocyclyl moiety;
CAR represents said ballasted carrier moiety; and
t is a positive integer of 1 to 2.

18. The photographic assemblage of claim 17 wherein t is 1, G is OH and Z represents the atoms necessary to complete a pyridine or pyrimidine ring.

19. The photographic assemblage of claim 17 wherein G is hydroxy; or an acyloxy group having the formula —OCOR$^1$, —OCOOR$^1$, or —OCON(R$^1$)$_2$, wherein R$^1$ is an alkyl group having 1 to about 8 carbon atoms or an aryl group having 6 to about 12 carbon atoms, or a group which together with

is CAR, said CAR being bonded to the naphthalene group through the oxygen of said

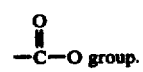

20. The photographic assemblage of claim 17 wherein said CAR is a group having the formula:

(Ballast-Carrier-Link)— wherein:
 (a) Ballast is an organic ballasting radical of such molecular size and configuration as to render said compound nondiffusible in said photographic assemblage during development in an alkaline processing composition;
 (b) Carrier is an oxidizable acyclic, carbocyclic or heterocyclic moiety; and
 (c) Link represents a group which upon oxidation of said carrier moiety is capable of being hydrolytically cleaved to release said diffusible dye.

21. The photographic assemblage of claim 20 wherein the Carrier moiety contains atoms according to the following configuration:

wherein:
b is a positive integer of 1 to 2; and
a represents the radicals OH, SH, NH—, or hydrolyzable precursors thereof.

22. The photographic assemblage of claim 16 wherein said dye image-receiving layer or a layer adjacent thereto contains metal ions.

23. The photographic assemblage of claim 22 wherein:
(a) said dye image-receiving layer is located between said support and said silver halide emulsion layer; and
(b) said assemblage also includes a transparent cover sheet over the layer outermost from said support.

24. The photographic assemblage of claim 23 wherein said cover sheet has thereon, in sequence, a neutralizing layer and a timing layer.

25. The photographic assemblage of claim 24 wherein said discharging means is a rupturable container containing said alkaline processing composition and an opacifying agent, said container being so positioned during processing of said assemblage that a compressive force applied to said container will effect a discharge of the container's contents between said transparent sheet and the layer outermost from said support.

26. The photographic assemblage of claim 22 wherein said support having thereon said photosensitive silver halide emulsion layer is opaque and said dye image-receiving layer is located on a separate transparent support superposed over the layer outermost from said opaque support.

27. The photographic assemblage of claim 26 wherein said transparent support has thereon, in sequence, a neutralizing layer, a timing layer, and said dye image-receiving layer.

28. In an integral photographic assemblage comprising:
(a) a photosensitive element comprising a transparent support having thereon the following layers in sequence: a dye image-receiving layer, an alkaline solution-permeable, light-reflective layer, an alkaline solution-permeable, opaque layer, a red-sensitive silver halide emulsion layer having a ballasted cyan dye releaser associated therewith, a green-sensitive silver halide emulsion layer having a ballasted magenta dye releaser associated therewith, and a blue-sensitive silver halide emulsion layer having a ballasted yellow dye releaser associated therewith;
(b) a transparent sheet superposed over said blue-sensitive silver halide emulsion layer and comprising a transparent support having thereon, in sequence, a neutralizing layer and a timing layer; and
(c) a rupturable container containing an alkaline processing composition and an opacifying agent which is so positioned during processing of said assemblage that a compressive force applied to said container will effect a discharge of the container's contents between said transparent sheet and said blue-sensitive silver halide emulsion layer; said assemblage containing a silver halide developing agent; the improvement wherein at least one of said ballasted dye releasers is a nondiffusible compound having at least one releasable 2-(2-heterocyclylazo)-1-naphthol dye moiety, said compound containing a ballasted carrier moiety which is capable of releasing said diffusible azo dye as a function of development of said silver halide emulsion layer under alkaline conditions, said heterocyclyl moiety containing a nitrogen atom adjacent to the point of attachment to the azo linkage, said heterocyclyl moiety not being substituted with a nitro group, and said heterocyclyl moiety being selected from the group consisting of pyridine, pyrimidine, quinoline, isoquinoline, pyrazine, pyridazine, thiazole, thiadiazole, triazole, benzothiazole and acinaphthothiazole.

29. The photographic assemblage of claim 28 wherein said compound has the formula:

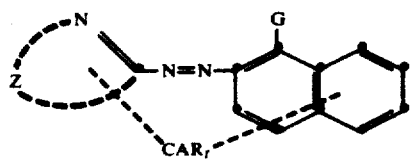

wherein:
G is a hydroxy group, a salt thereof, or a hydrolyzable precursor thereof; or a group which together with

is CAR, said CAR being bonded to the naphthalene group through the oxygen or said

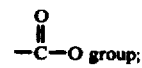 group;

Z represents the atoms necessary to complete said heterocyclyl moiety;
CAR represents said ballasted carrier moiety; and
t is a positive integer of 1 to 2.

30. The photographic assemblage of claim 28 wherein said dye image-receiving layer or a layer adjacent thereto contains metal ions.

31. A process for producing a photographic transfer image in color in an imagewise-exposed photographic element comprising a support having thereon at least one photosensitive silver halide emulsion layer, said emulsion layer having associated therewith a nondiffusible compound having at least one releasable 2-(2-heterocyclylazo)-1-naphthol dye moiety, said compound containing a ballasted carrier moiety which is capable of releasing said diffusible azo dye as a function of development of said silver halide emulsion layer under alkaline conditions, said heterocyclyl moiety containing a nitrogen atom adjacent to the point of attachment to the azo linkage, said heterocyclyl moiety not being substituted with a nitro group, and said heterocyclyl moiety being selected from the group consisting of pyridine, pyrimidine, quinoline, isoquinoline, pyrazine, pyridazine, thiazole, thiadiazole, triazole, benzothiazole and acinaphthothiazole, said process comprising:

(1) treating said photographic element with an alkaline processing composition in the presence of a silver halide developing agent to effect development of each of the exposed silver halide emulsion layers;

(2) said dye-releasing compound then releasing said diffusible azo dye imagewise as a function of said development of each of said silver halide emulsion layers;

(3) at least a portion of said imagewise distribution of said azo dye diffusing to a dye image-receiving layer; and (4) contacting said imagewise distribution of said azo dye in said dye image-receiving layer with metal ions, thereby forming a metal-complexed, azo dye transfer image.

32. The process of claim 31 wherein said nondiffusible compound has the formula:

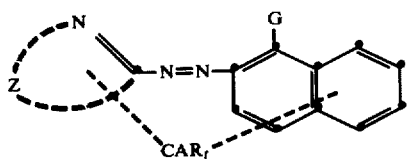

wherein:

G is a hydroxy group, a salt thereof, or a hydrolyzable precursor thereof; or a group which together with

is CAR, said CAR being bonded to the naphthalene group through the oxygen of said

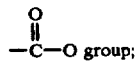 group;

Z represents the atoms necessary to complete said heterocyclyl moiety;

CAR represents said ballasted carrier moiety; and t is a positive integer of 1 to 2.

33. A process for producing a photographic transfer image in color in an imagewise-exposed photographic element comprising a support having thereon at least one photosensitive silver halide emulsion layer, said emulsion layer having associated therewith a nondiffusible compound having at least one releasable 2-(2-heterocyclylazo)-1-naphthol dye moiety, said compound containing a ballasted carrier moiety which is capable of releasing said diffusible azo dye as a function of development of said silver halide emulsion layer under alkaline conditions, said heterocyclyl moiety containing a nitrogen atom adjacent to the point of attachment to the azo linkage, said heterocyclyl moiety not being substituted with a nitro group, and said heterocyclyl moiety being selected from the group consisting of pyridine, pyrimidine, quinoline, isoquinoline, pyrazine, pyridazine, thiazole, thiadiazole, triazole, benzothiazole and acinaphthothiazole, said ballasted carrier moiety being a group having the formula:

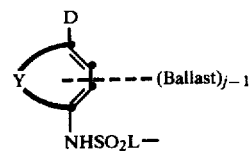

wherein:

(a) Ballast is an organic ballasting radical of such molecular size and configuration as to render said compound nondiffusible in said photographic element during development in an alkaline processing composition;

(b) D is $OR^2$ or $NHR^3$ wherein $R^2$ is hydrogen or a hydrolyzable moiety and $R^3$ is hydrogen or a substituted or unsubstituted alkyl group of 1 to 22 carbon atoms;

(c) Y represents the atoms necessary to complete a benzene nucleus, a naphthalene nucleus or a 5- to 7-membered heterocyclic ring;

(d) j is a positive integer from 1 to 2 and is 2 when D is $OR^2$ or when $R^3$ is hydrogen or an alkyl group of less than 8 carbon atoms; and (e) L is a linking group which is $[X—(NR^4—J)_q]_m—$ or $X—J—NR^4—$ wherein:

(i) X represents a bivalent linking group of the formula $—R^5—L'_n—R^5_p—$ where each $R^5$ can be the same or different and each represents an alkylene radical having 1 to about 8 carbon atoms; a phenylene radical; or a substituted phenylene radical having 6 to about 9 carbon atoms;

(ii) L' represents a bivalent radical selected from oxy, carbonyl, carboxamido, carbamoyl, sulfonamido, ureylene, sulfamoyl, sulfinyl or sulfonyl;

(iii) n is an integer of 0 or 1;

(iv) p is 1 when n equals 1 and p is 1 or 0 when n equals 0, provided that when p is 1 the carbon content of the sum of both $R^5$ radicals does not exceed 14 carbon atoms;

(v) $R^4$ represents a hydrogen atom, or an alkyl radical having 1 to about 6 carbon atoms;

(vi) J represents a bivalent radical selected from sulfonyl or carbonyl;

(vii) q represents an integer of 0 or 1; and (viii) m represents an integer of 0, 1 or 2; said process comprising:

(1) treating said photographic element with an alkaline processing composition in the presence of a silver halide developing agent to effect development of each of the exposed silver halide emulsion layers, thereby oxidizing said developing agent;

(2) said oxidized developing agent thereby cross-oxidizing said dye-releasing compound;

(3) said cross-oxidized dye-releasing compound then cleaving as a result of alkaline hydrolysis to release said diffusible azo dye imagewise as a function of said imagewise exposure of each of said silver halide emulsion layers;

(4) at least a portion of said imagewise distribution of said azo dye diffusing to a dye image-receiving layer; and (5) contacting said imagewise distribution of said azo dye with metal ions, thereby forming a metal-complexed, azo dye transfer image.

34. The process of claim 33 wherein D is OH, j is 2, Y is a naphthalene nucleus, G is OH and t is 1.

35. The photographic element of claim 2 wherein t is 1, G is OH and Z represents the atoms necessary to complete a pyridine, pyrimidine, pyrazine, quinoline or isoquinoline ring.

36. The photographic assemblage of claim 17 wherein t is 1, G is OH, and Z represents the atoms necessary to complete a pyridine, pyrimidine, pyrazine, quinoline or isoquinoline ring.

* * * * *